US006753965B2

(12) United States Patent
Kumar et al.

(10) Patent No.: US 6,753,965 B2
(45) Date of Patent: Jun. 22, 2004

(54) DEFECT DETECTION SYSTEM FOR QUALITY ASSURANCE USING AUTOMATED VISUAL INSPECTION

(75) Inventors: Ajay Kumar, Kanpur (IN); Kwok-Hung Grantham Pang, Hong Kong (CN)

(73) Assignee: The University of Hong Kong (CN)

( * ) Notice: Subject to any disclaimer, the term of this patent is extended or adjusted under 35 U.S.C. 154(b) by 363 days.

(21) Appl. No.: 10/144,588

(22) Filed: Oct. 25, 2001

(65) Prior Publication Data

US 2003/0081215 A1 May 1, 2003

Related U.S. Application Data

(60) Provisional application No. 60/260,520, filed on Jan. 9, 2001.

(51) Int. Cl.[7] .......................... G01N 21/84; G01N 21/00
(52) U.S. Cl. .................. 356/431; 356/238.1; 356/238.2
(58) Field of Search ................................ 356/429, 430, 356/431, 238.1, 238.2

(56) References Cited

U.S. PATENT DOCUMENTS

| | | | | |
|---|---|---|---|---|
| 4,630,304 A | | 12/1986 | Borth et al. ................... | 381/94 |
| 5,301,129 A | * | 4/1994 | McKaughan et al. ........ | 382/149 |
| 5,737,072 A | | 4/1998 | Emery et al. .................. | 365/73 |
| 5,740,048 A | | 4/1998 | Abel et al. ................... | 364/443 |
| 5,774,177 A | * | 6/1998 | Lane ............................ | 348/88 |
| 5,825,501 A | | 10/1998 | Mee et al. .................... | 356/429 |

FOREIGN PATENT DOCUMENTS

EP          0 974 831 A2    1/2000

OTHER PUBLICATIONS

Partial European Search Report for EP 01 10 9375 dated Jun. 22, 2001.

Abdulghafour et al., "Non–deterministic Approaches in Date Fusion—A Review," *SPIE* 1383:596–610 (1990).

Beck et al., "Spatial Frequency Channels and Perceptual Grouping in Texture Segregation," *Comput. Vis. Graph. Image Process.*, 37: 299–325 (1987).

Bovik et al., "Multichannel Texture Analysis Using Localized Spatial Filters," *IEEE Trans. Pattern Anal. Mach. Intell.*, 12(1):55–73 (1990).

Casasent et al., "Detection Filters and Algorithm Fusion for ATR," *IEEE Trans. Image Process.*, 6(1):114–125 (1997).

(List continued on next page.)

*Primary Examiner*—Frank G. Font
*Assistant Examiner*—Roy M. Punnoose
(74) *Attorney, Agent, or Firm*—Dickstein, Shapiro, Morin & Oshinsky, LLP.

(57) ABSTRACT

A defect detection method and system for the automated visual inspection of web materials is provided. The invention utilize real Gabor function (RGF) filters with a non-linear function for estimating the local energy. An example method for quality assurance using automated visual inspection in accordance with the invention includes the steps of: automated design of a bank of RGF filters; using these RGF filters to sample the features of image under inspection; using a non-linear function to compute local energy estimate in the filtered images; combining all the filtered images using image fusion; and finally thresholding the resultant image to segment the defects in the inspection image. Possible embodiments of the described invention include detection of only a class of defects using a single tuned real Gabor filter or a bank of real Gabor functions.

36 Claims, 22 Drawing Sheets

OTHER PUBLICATIONS

Figure 1:
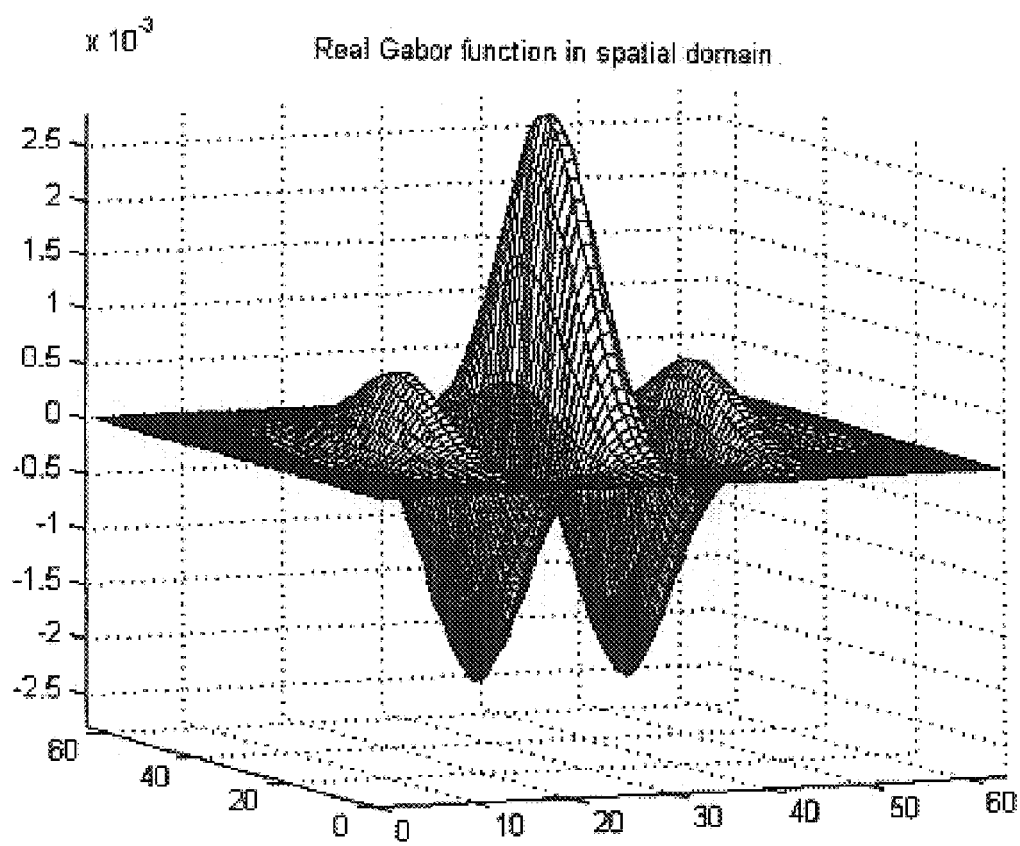

Casasent, "Gabor Wavelet Filters and Fusion for Distortion–Invariant Multi–Class Object Detection," *Proc. SPIE*, 2491:430–440 (1995).

Casasent, "Neural net design of macro Gabor wavelet filters for distortion–invariant object detection in clutter," *Opt. Eng.*, 33(7):2264–2271 (1994).

Casasent et al., "Real, imaginary, and clutter Gabor filter fusion for detection with reduced false alarms," *Opt. Eng.*, 33(7):2255–2363 (1994).

Chan et al., "Fabric Defect Detection by Fourier Analysis," *IEEE Trans. Ind. Appl.*, 36(5):1267–1276 (2000).

Cohen et al., "Automated Inspection of Textile Fabrics Using Textural Models," *IEEE Trans. Anal. Mach.*, 13(8):803–808 (1991).

Crounse et al., "Methods for Image Processing and Pattern Formation," *IEEE Trans. Circuits Syst., I–Fundam. Theory Appl.*, 42(10):583–601 (1995).

Escofet et al., "Detection of local defects in textile webs using Gabor filters," *Opt. Eng.*, 37(8):2297–2307 (1998).

Escofet et al., "Detection of Local Defects in Textile Webs Using Gabor Filters," *Proc. SPIE*, 2785:163–170 (1996).

Jain et al., "Learning Texture Discrimination Masks," *IEEE Trans. Pattern anal. Mach. Intell.*, 18(2):195–205 (1996).

Jain et al., "Unsupervised Texture Segmentation Using Gabor Filters," *Pattern Recogn.*, 24(12):1167–1169 (1991).

Julesz, "Textons, the elements of texture perception, and their interactions," *Nature London*, 290:91–97 (1981).

Namuduri et al., "Efficient Computation of Gabor Filter Based Multiresolution Response," *Pattern Recogn.*, 27(7):925–938 (1994).

Oe, "Texture Segmentation Method by Using Two–Dimensional AR Model and Kullback Information," *Pattern Recogn.*, 26(2):237–244 (1993).

Pollen et al., "Visual Cortical Neurons as Localized Spatial Frequency Filters," *IEEE Trans. Syst. Man Cybern.*, 13(5):907–916 (1983).

Portilla et al., "Texture synthesis–by analysis method based on a multiscale early–vision model," *Opt. Eng.*, 35(8):2403–2417 (1996).

Randen et al., "Filtering for Texture Classification: A Comparative Study," *IEEE Trans. Pattern Anal. Mach. Intell.*, 21(4):291–310 (1999).

Rodriguez–Sanchez et al., "The RGFF Representation Model: A System for the Automatically Learned Partitioning of 'Visual Patterns' in Digital Images," *IEEE Trans. Patern Anal. Mach. Intell.*, 21(10):1044–1073 (1999).

Sari–Sarraf et al., "Vision System for On–Loom Fabric Inspection," *IEEE Trans. Ind. Appl.*, 35(6):1252–1259 (1999).

Shi, "Gabor–Type Image Filtering with Cellular Neural Networks," *IEEE International Symp. On Circuits and Systems, ISCAs '96*, 3:558–561 (1996).

Sutter et al., "Contrast and spatial variables in texture segregation: Testing a simple spatial–frequency channels model," *Percept. Psychophys.*, 46(4):312–332 (1989).

Talukder et al., "General methodology for simultaneous representation and discrimiation of multiple object classes," *Opt. Eng.*, 37(3):904–917 (1998).

Talukder et al., "Nonlinear Feaures for Classification and Pose Estimation of Machine Parts from Single Views," *Proc. SPIE*, 3522:16–27 (1998).

Talukder et al., "Pose Estimation and Transformation of Faces," *Proc. SPIE*, 3522:84–95 (1998).

Tsai et al., "Applying an Artificial Neural Network to Pattern Recognition in Fabric Defects," *Text. Res. J.*, 65(3):123–130 (1995).

Unser et al., "Feature extraction and decision procedure for automated inspection of texture materials," *Pattern. Recogn. Lett.*, 2:181–191 (1984).

Unser et al., "Nonlinear Operators for Improving Texture Segmentation Based on Features Extracted by Spatial Filtering," *IEEE Trans. Syst. Man. Cybern.*, 20(4):804–815 (1990).

Weber et al., "Fusion and optimized Gabor filter design for object detection," *Proc. SPIE*, 2588:662–675 (1995).

Weber et al., "Quadralic Gabor filters for object detection," *Proc. 1997 South African Symp. On Communications and Signal Processing*, 69–74 (1997).

Wood, "Applying Fourier and Associated Transforms to Pattern Characterization in Textiles," *Text Res. J.*, 60:212–220 (1990).

Zhang et al., "Fabric Defect Detection and Classification Using Image Analysis," *Text Res. J.*, 65(1):1–9 (1995).

* cited by examiner

DEFECT DETECTION SYSTEM FOR QUALITY ASSURANCE USING AUTOMATED VISUAL INSPECTION

CROSS-REFERENCE TO RELATED APPLICATIONS

This application claims priority to the provisional U.S. patent application Ser. No. 60/260,520 filed on Jan. 9, 2001 by Kumar et al. In addition, the disclosure of the U.S. patent application Ser. No. 09/837,065 filed on Apr. 18, 2001 is incorporated herein in its entirety.

FIELD OF THE INVENTION

The present invention relates to a method and system for automated visual monitoring of surface characteristics, and more particularly to automated optical inspection of textile characteristics to detect fabric defects and anomalies.

BACKGROUND OF THE INVENTION

The development of a reliable automated visual inspection system for quality assurance requires extensive research and development effort. Human inspectors typically perform visual inspection for quality assurance in industrial products. The disadvantage with the manual inspection are: (1) low speed, (2) high cost, (3) inability to perform real-time inspection and, (4) the serious limitations on the range of detectable defects. Therefore, automation of visual inspection process can improve the efficiency of production lines by overcoming at least one of the aforesaid drawbacks.

Automated visual inspection of industrial web materials has extremely high requirements as compared to other inspection problems. Generally the width of industrial web is about 1.6–2.0 meters and requires an array of CMOS/CCD photosensors to inspect the web that is moving at the speed of 10–15 meters per minute. Consequently the throughput for 100% inspection is tremendous (10–15 MB image data per second when using line-scan cameras) and therefore most feasible solutions require additional DSP hardware components and reduction in computational complexity.

Prior researchers have attempted to create visual inspection systems using different approaches. Researchers have frequently used textile web samples to model the general problem of defect detection in various textured materials. Segmentation of fabric defects from the inspection images using the edge detection, mean and standard deviations of sub blocks, gray level co-occurrence matrix, and autocorrelation of images and, Karhunen-Loeve transform has been detailed in the literature. Solutions to defect detection problems using various texture analysis approaches include Gauss Markov Random Field (GMRF) modeling, Gabor filters, Wavelet transform, and Optical Fourier transform.

The periodic structure of woven web materials provides valuable information, and therefore Fourier domain features have been used in the fabric defect detection. This approach is extensively detailed in U.S. Pat. No. 4,124,300 issued on Nov. 7, 1976. When defects cause global distortions in woven web materials, Fourier analysis is most suitable. But this is not true for local fabric defects and therefore techniques that can simultaneously measure in spatial and spatial-frequency domain are more useful. U.S. Pat. No. 5,815,198 issued in December 1998 discloses a multi-scale wavelet decomposition of web images for fabric defect detection. The disadvantage with the techniques based on multiscale wavelet decomposition is that the wavelet bases (unlike RGF) are shift variant. Therefore, it is difficult to characterize a texture pattern from the wavelet coefficients since the wavelet descriptors depend on pattern location.

Additional examples include the U.S. Pat. No. 5,665,907 issued on Sep. 9, 1997 to the University of Chicago providing an ultrasonic system to detect fabric defects. Another recent U.S. Pat. No. 6,023,334 issued on Feb. 8, 2000 to Toshiba Engineering Corp. discloses an alternative approach based on brightness information, suited to inspection of homogenous surface like plain aluminum sheet or plain glass.

The aforementioned approaches suffer from various drawbacks such as the limited range of detectable defects, the extent of required computational and other resources as well as the need for further automation.

SUMMARY OF THE INVENTION

The present invention provides a new approach for defect detection using real Gabor function (RGF) filters that overcomes one or more of the drawbacks noted in the context of previous approaches. Thus, some defects that only alter the gray level arrangement of neighboring pixels (such as mispick in textile web) cannot be detected with the techniques based on mean and standard deviations of image sub-blocks. In light of the preceding, a multi-channel filtering approach to segment, i.e., identify, both fine and coarse texture defects is found to be useful as is shown later. This is achieved by segmenting the fine and coarse defects with the RGF filters of different scales (multichannel).

In an aspect of the invention, an embodiment of the invention uses real Gabor functions instead of complex Gabor function, thus, halving the computational time for the computation of the filtered images. Advantageously, the real Gabor function acts as a blob detector. In many embodiments of the invention, the real and imaginary parts of Gabor function are Hilbert pairs, thus, reducing the need for the imaginary part.

In another aspect, an embodiment of the invention enables automated selection of center frequency of real Gabor function using fast Fourier transform (FFT). Thus, change in the texture background under the inspection requires little or no manual tuning.

In another aspect, an embodiment of the invention exhibits superior computational and performance gain by the usage of non-linear function to estimate the local energy in the course of detecting defects.

Moreover, many embodiments of the invention employ the image fusion technique based on the Bernouli's rule of combination for integrating information from different channels to improve the detection rate while reducing false alarms.

In yet another aspect, the invention enhances computational efficiency by a judicious choice of thresholds and convolution masks to reflect appropriate trade-offs. Moreover, a simple thresholding method removes isolated noisy pixels without requiring any morphological operations.

LIST OF FIGURES

FIG. 1. Perspective view of real Gabor function in spatial domain.

Figure 2:
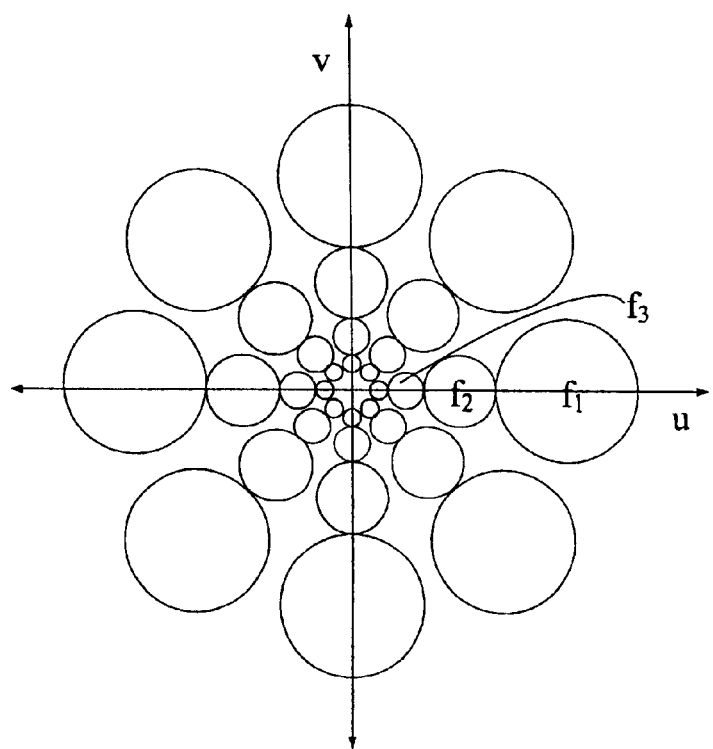

FIG. 2. Frequency domain representation of 16 Gabor filters on log-polar scale.

Figure 3:
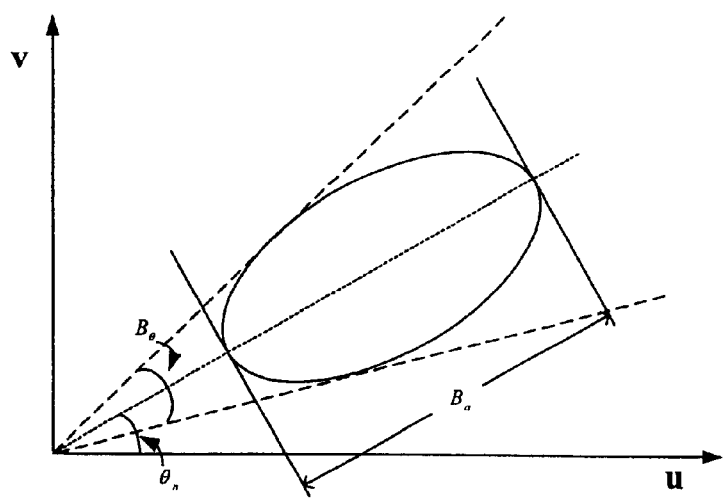

FIG. 3. Frequency domain parameters of a Gabor filter.

Figure 4:
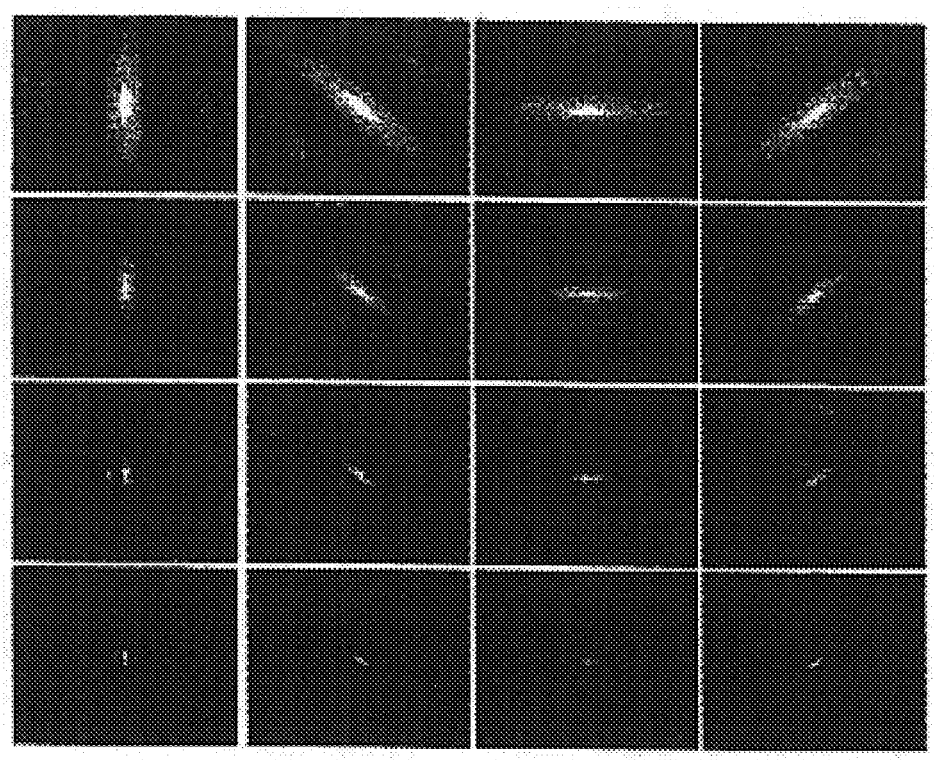

FIG. 4. Sixteen Real Gabor functions in spatial domain.

Figure 5:
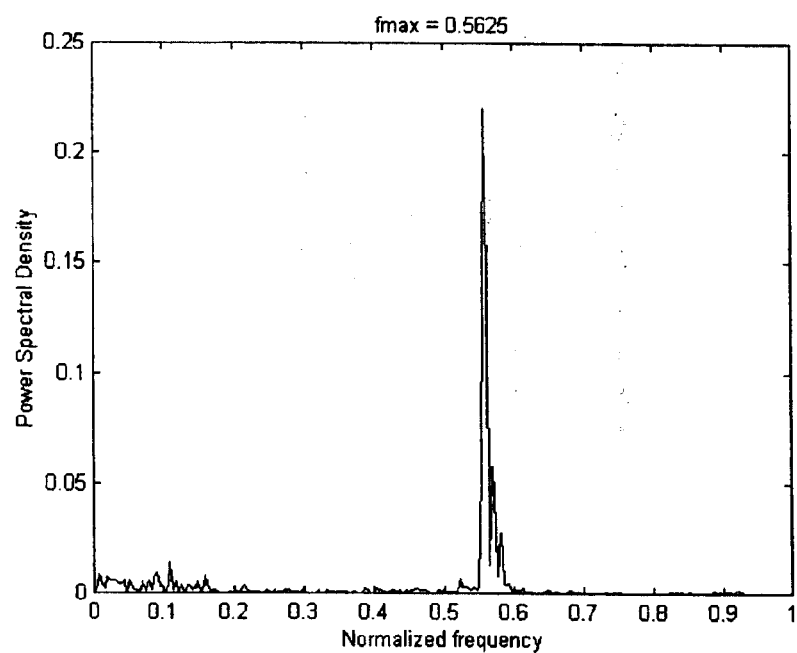

FIG. 5. Power spectral density from an example reference image for automatic selection of center frequency for real Gabor function.

Figure 6:
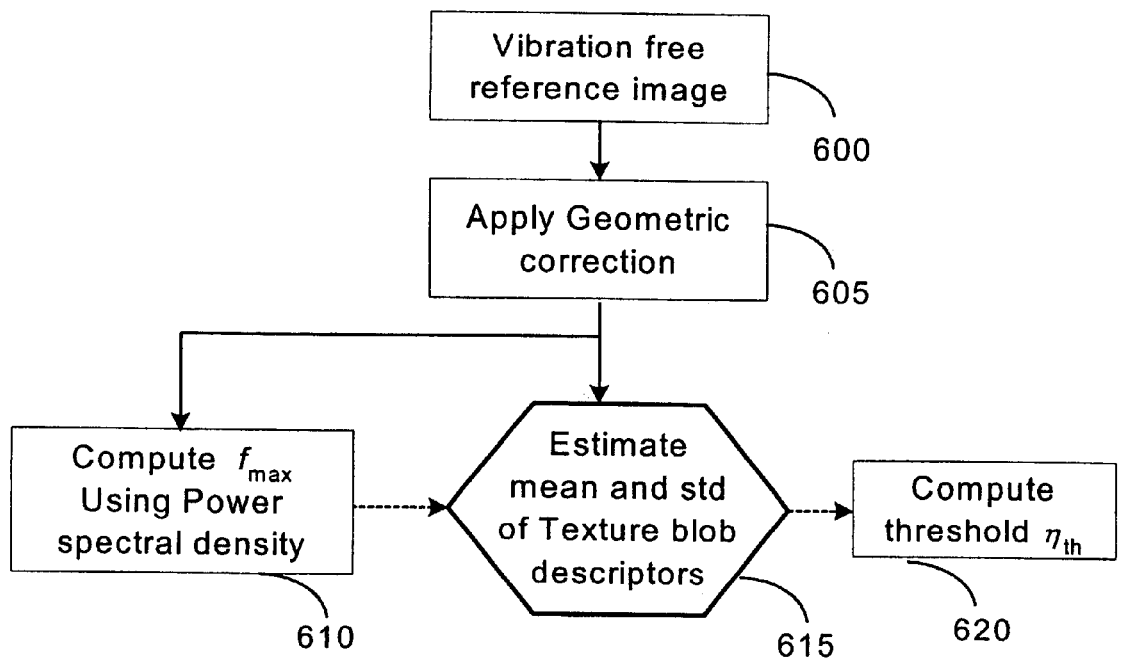

FIG. 6. Calculation of off-line parameters from a reference image.

Figure 7:
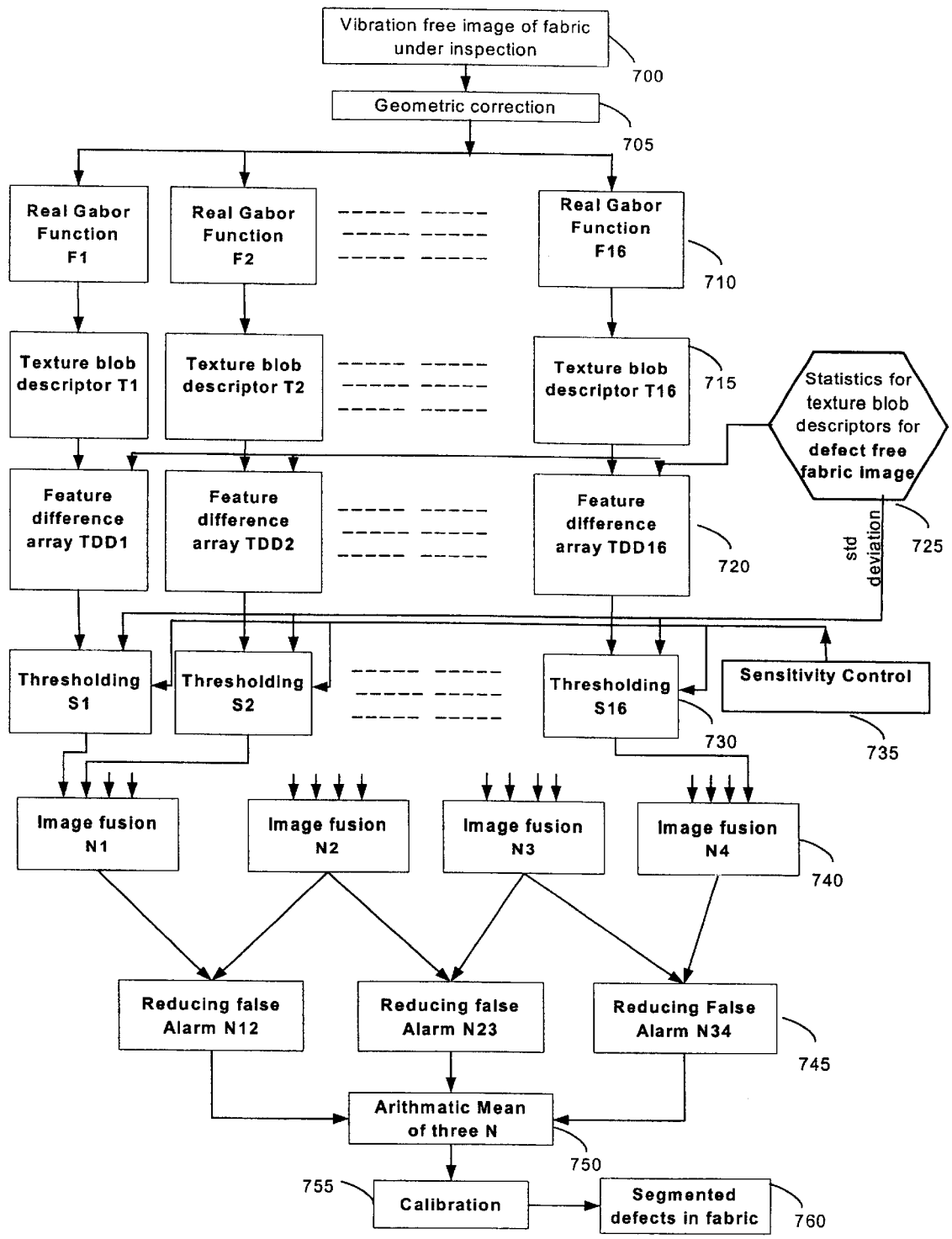

FIG. 7. Flowchart illustrating processing and steps in an on-line defect segmentation embodiment of the invention.

FIG. 8. Supervised defect segmentation: test sample A with its corresponding Gabor filtered images B and binarized filtered images with segmented defects C.

FIG. 9. Supervised defect segmentation: test sample A with its corresponding Gabor filtered images B and binarized filtered images with segmented defects C.

Figure 10A:
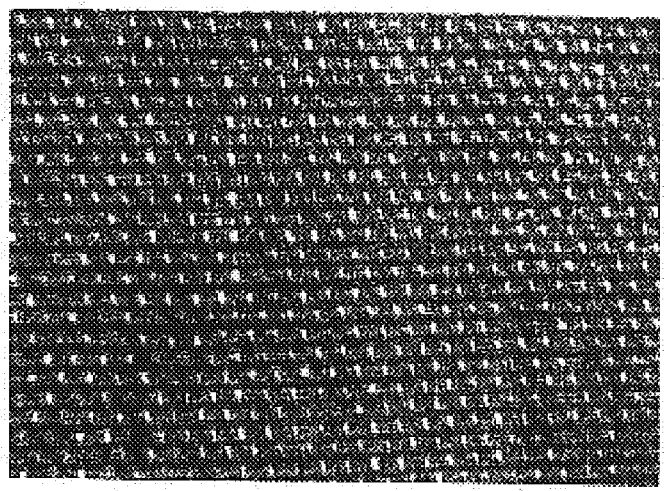
Figure 10B:
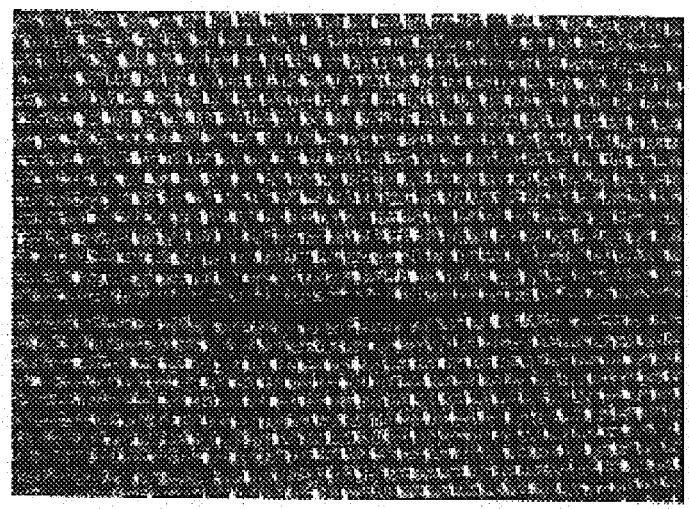
Figure 10C:
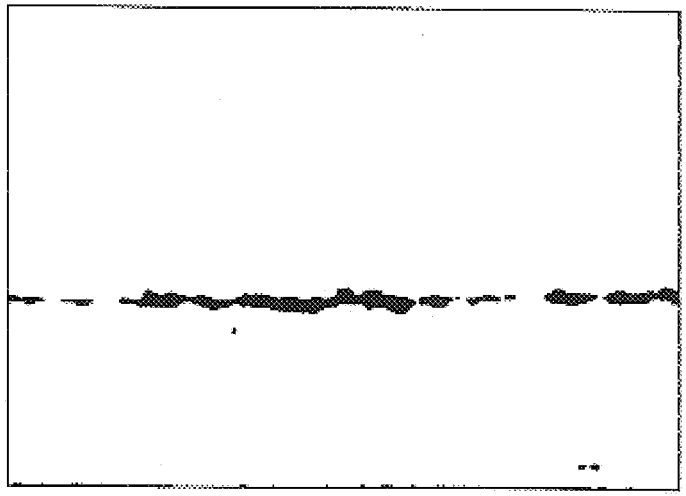

FIG. 10. Fabric sample for test: without defect (A), segmented defects, (B) with defects (C).

Figure 11A:
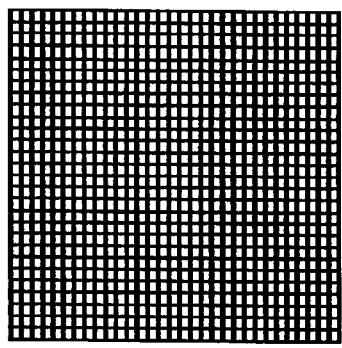
Figure 11B:
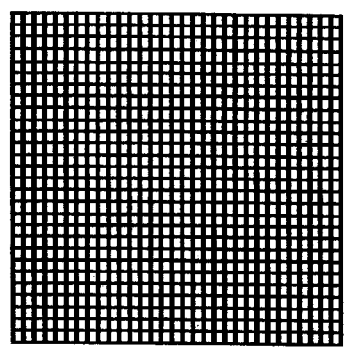
Figure 11C:
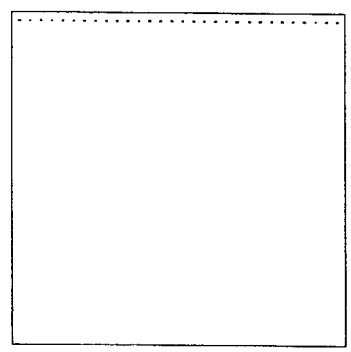
Figure 12A:
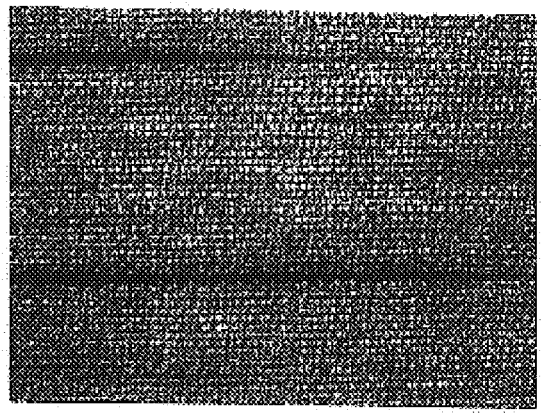
Figure 12B:
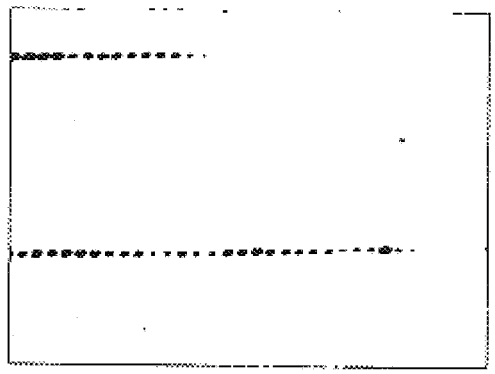
Figure 12C:
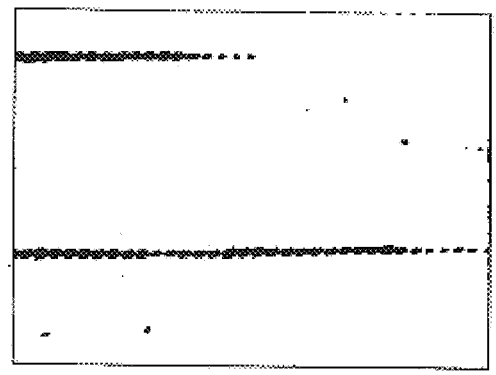
Figure 12D:
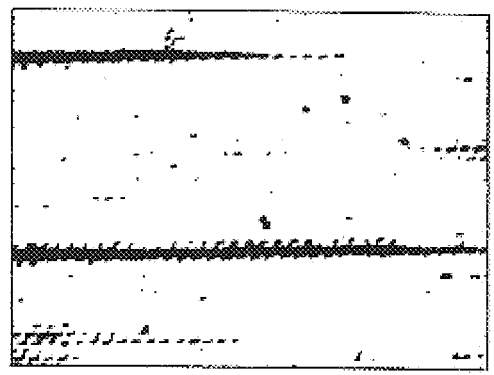

FIG. 11. Synthetic test fabric for evaluation: without defect (A), with defect (B) and, segmented defects (C).

FIG. 12. Fabric sample with defects (A) with its corresponding segmented defects at low (B), medium (C), and high sensitivity (D).

FIG. 13. Fabric sample with defects (A) and its corresponding binarized segmented defect (B).

Figure 14A:
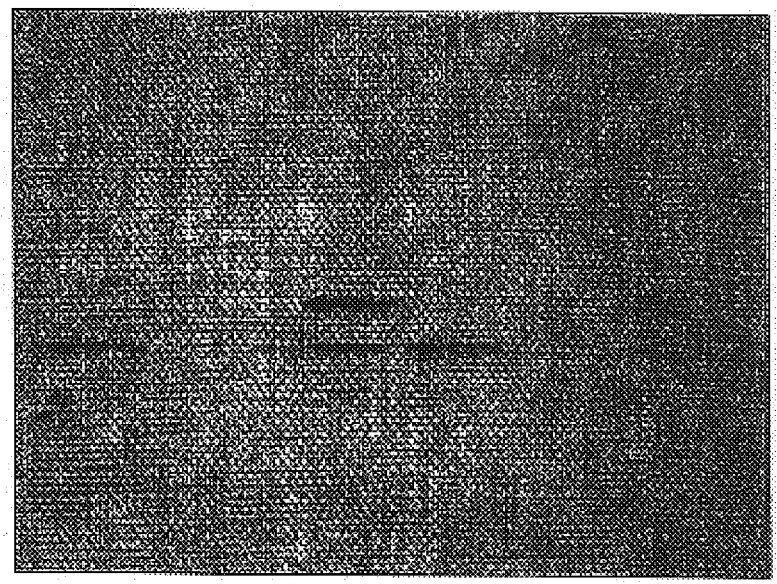

FIG. 14. Fabric sample with defects (A) and its corresponding binarized segmented defect (B).

Figure 15A:
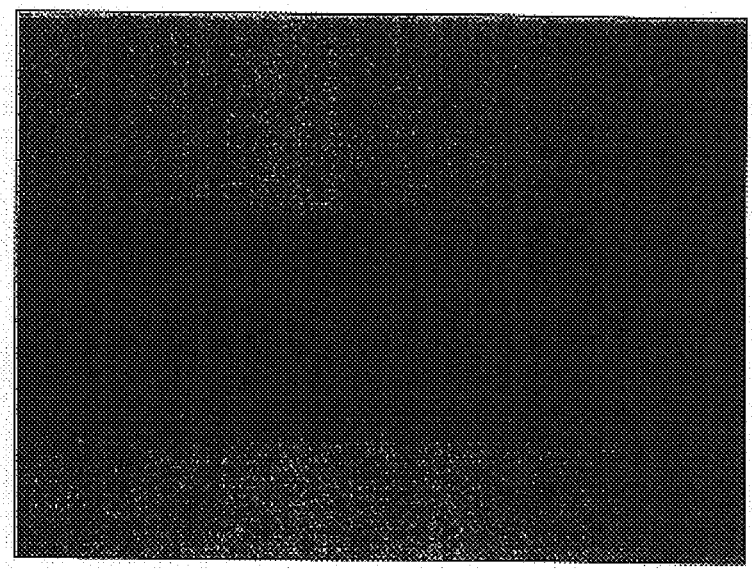
Figure 15B:
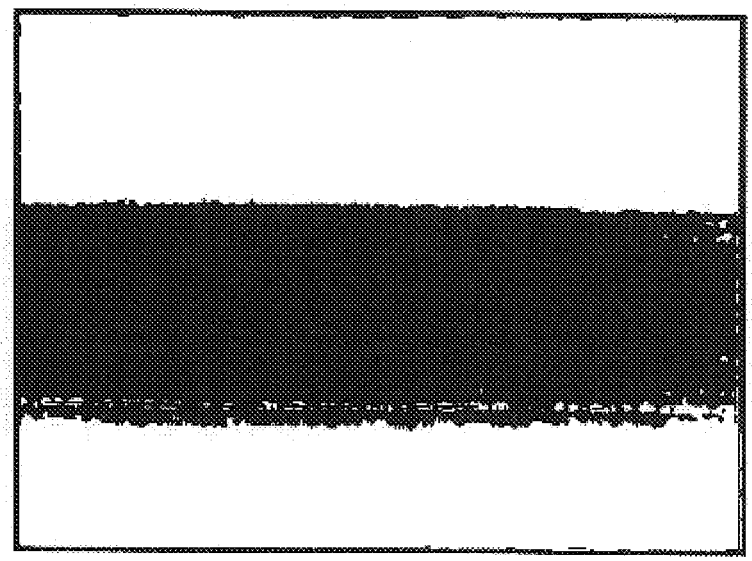

FIG. 15. Fabric sample with defects (A) and its corresponding binarized segmented defect (B).

Figure 16A:
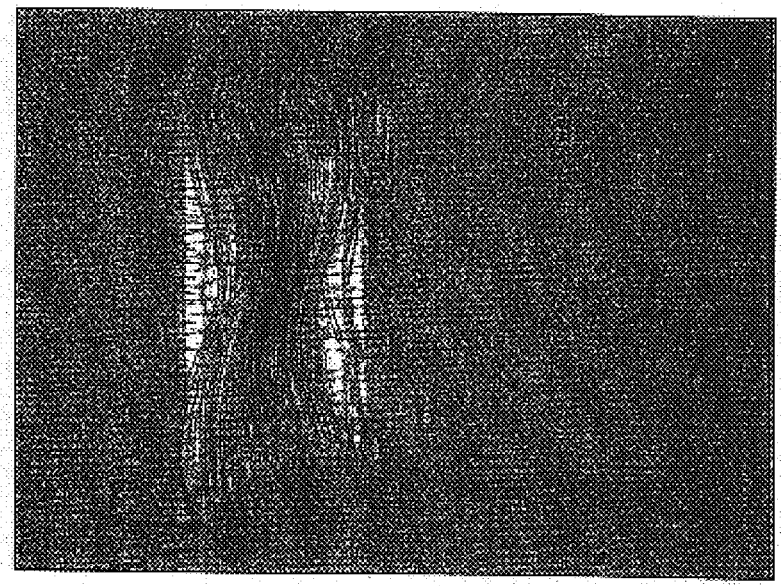
Figure 16B:
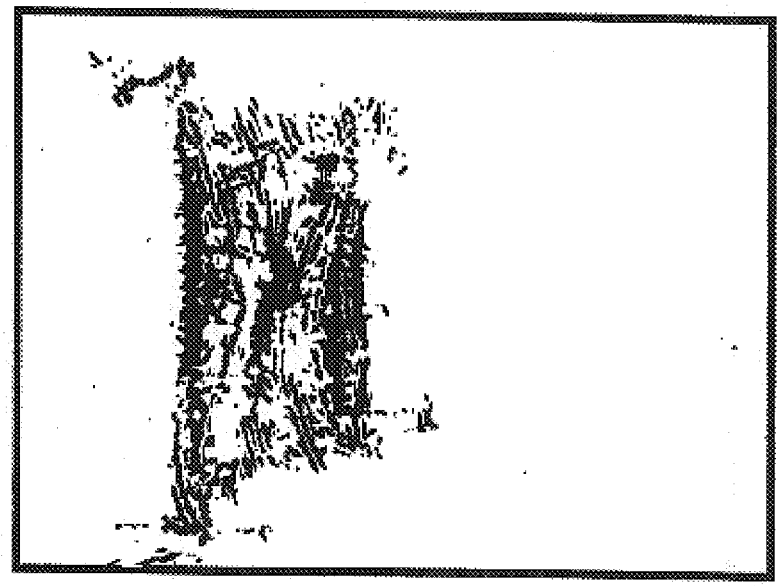

FIG. 16. Fabric sample with defects (A) and its corresponding binarized segmented defect (B).

Figure 17A:
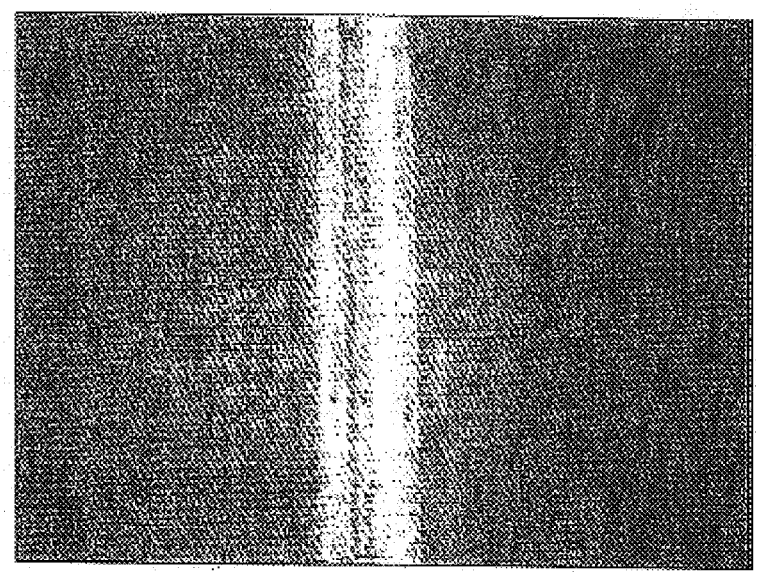

FIG. 17. Fabric sample with defects (A) and its corresponding binarized segmented defect (B).

Figure 18A:
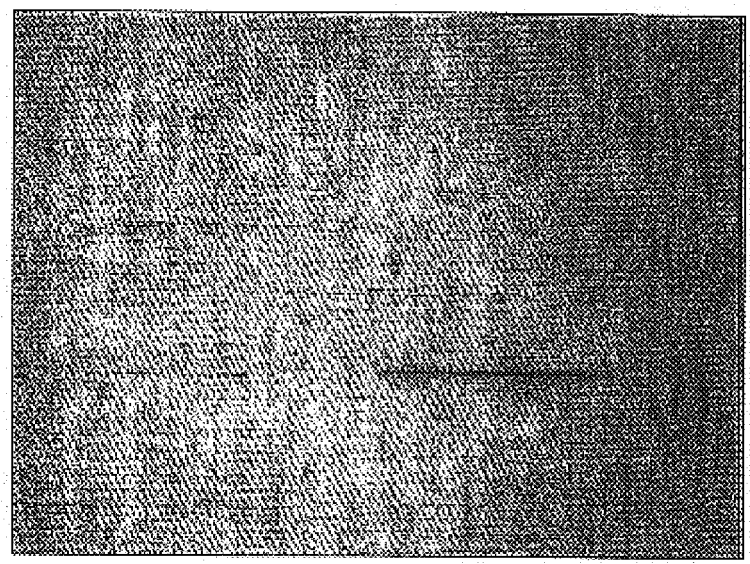
Figure 18B:
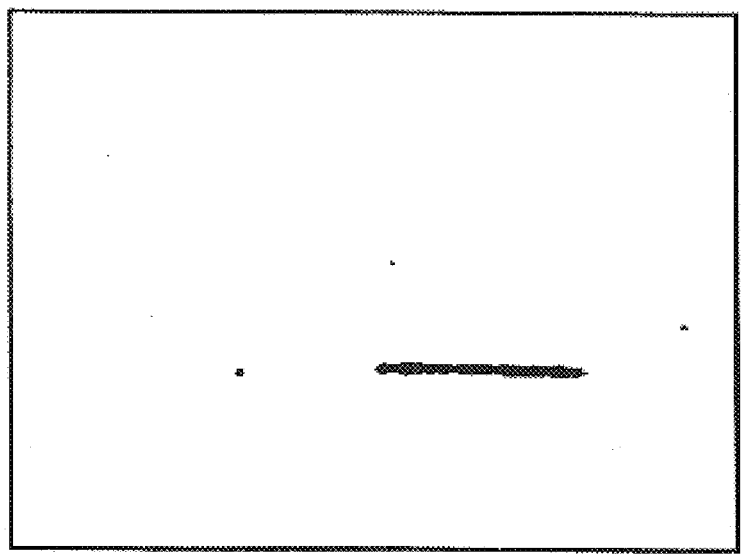

FIG. 18. Fabric sample with defects (A) and its corresponding binarized segmented defect (B).

Figure 19A:
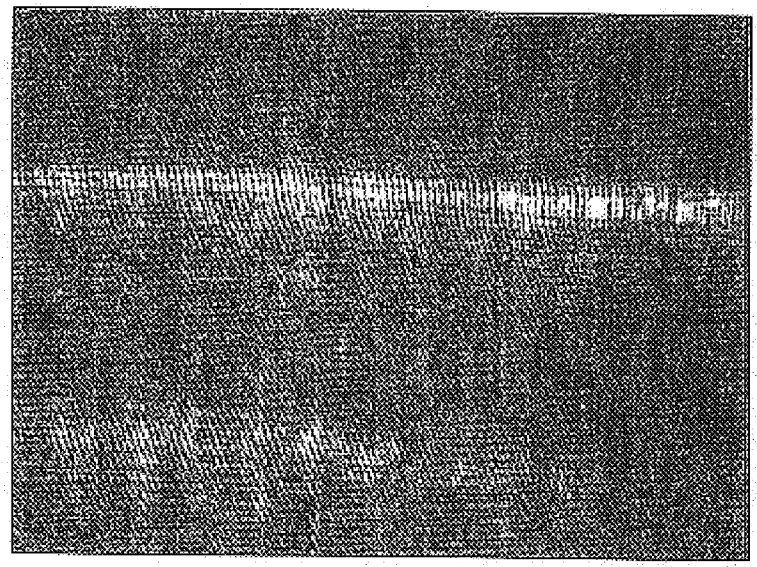
Figure 19B:
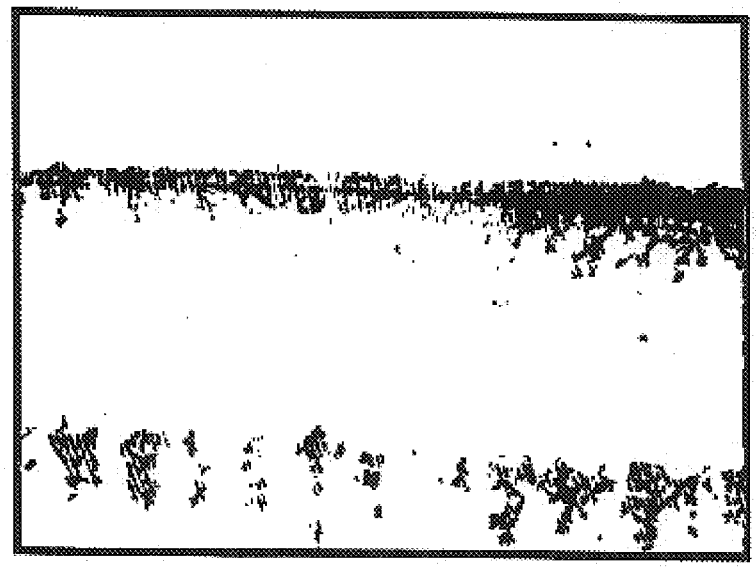

FIG. 19. Fabric sample with defects (A) and its corresponding binarized segmented defect (B).

FIG. 20. Fabric sample with defects (A) and its corresponding binarized segmented defect (B).

Figure 21A:
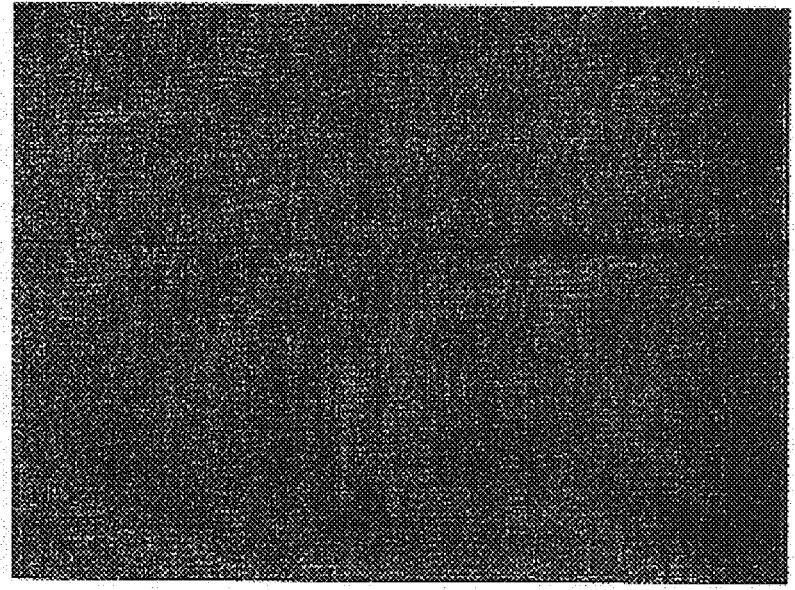
Figure 21B:
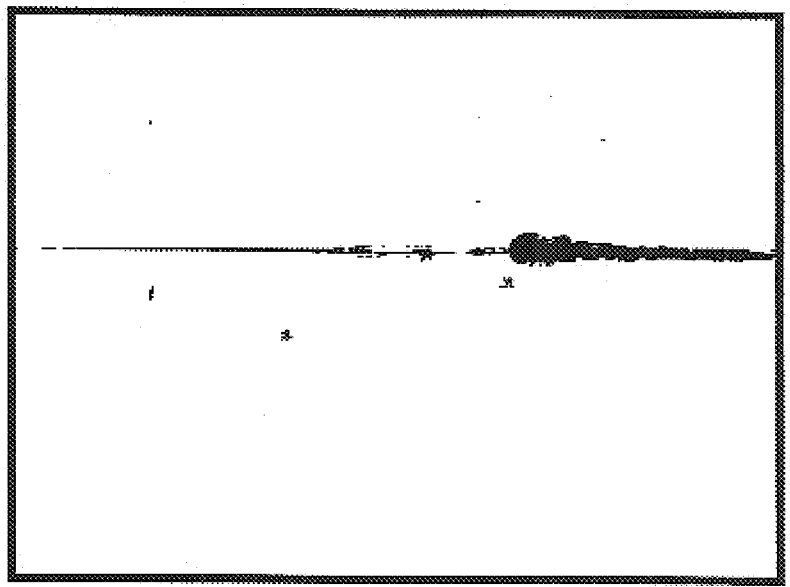

FIG. 21. Fabric sample with defects (A) and its corresponding binarized segmented defect (B).

Figure 22:
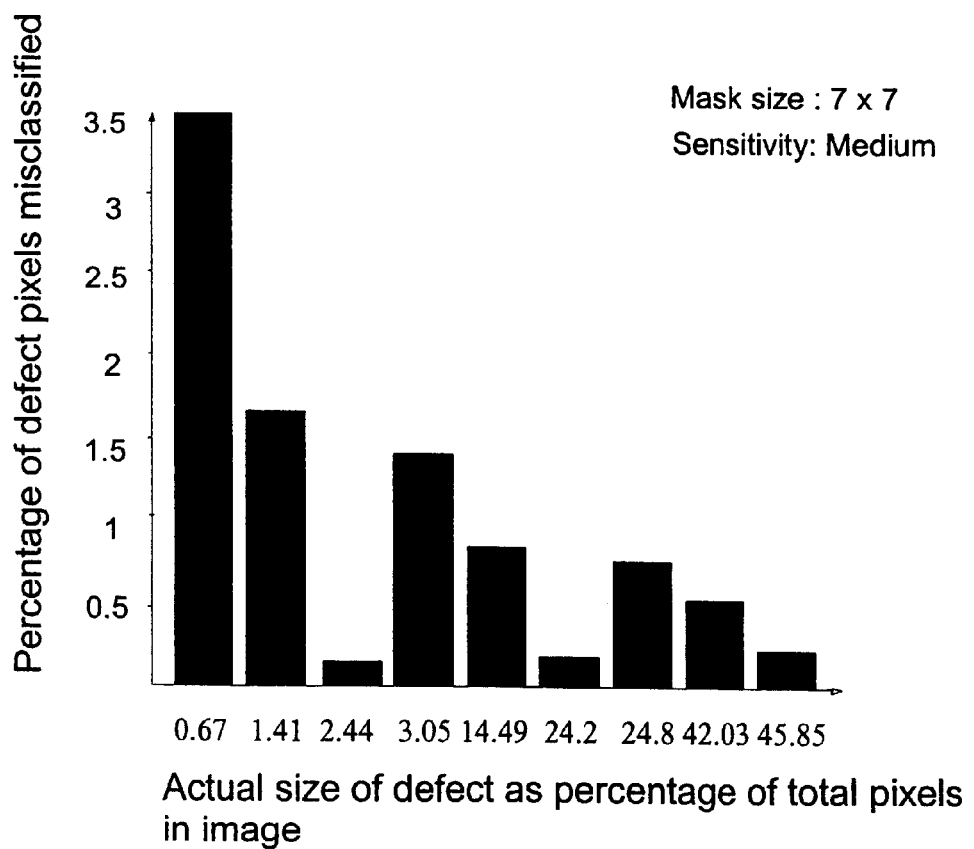

FIG. 22. Performance Analysis as a function of defect size.

DETAILED DESCRIPTION OF THE INVENTION

Two of the elements in the present invention, namely Real Gabor function and nonlinearity, are similar, in some respects, to the mechanisms in the visual cortex of mammals. This is not surprising since, for instance, phychophysically observed spatial-frequency channels and neurophysiologically observed blob-, bar- and edge-sensitive neurons have been used to explain texture perception in human vision. Some researchers have attempted to model for pretentative texture discrimination based on human visual mechanism. They have shown that the odd-symmetric (imaginary Gabor function) and even-symmetric (real Gabor function) filters differ in texture discrimination. For instance, odd-symmetric filters are not useful in texture discrimination unlike even-symmetric filters. Thus, they excluded odd-symmetric filters since they could not find any texture pair for which odd-symmetric mechanism was necessary.

Defect detection by human visual system depends on its nonlinearity. This nonlinearity, due to retinal adaptations, follows a simple-cell response (Gabor shaped) stage, thus, enabling human visual system to respond to local contrast over ten log units of illumination changes. There are at least two physiologically plausible explanations for this nonlinearity. First, non-linear contrast response function that typically has sigmoid shape with neurons that exhibit a threshold effect for low contrast and a saturation effect for higher contrast. Second, intra-cortical inhibition occurring within and among responses in different channels. Unlike prior researchers' preference for intra-cortical inhibition, we find that the non-linear contrast response function is well suited for defect detection.

Notably in the following description, 'complex Gabor function' or 'Gabor function' or 'Gabor filter' refers to the combined real and imaginary parts of Gabor function. Accordingly, 'real Gabor function' represents the real part of Gabor function and 'imaginary Gabor function' represents the imaginary part of Gabor function.

A Gabor function is a complex exponential modulated by a Gaussian function in the spatial domain, and is a shifted Gaussian in the frequency domain. In general, n-dimensional Gabor function is expressed as:

$$h(p) = f(p)m(p) \tag{1}$$

where $f(p)$ is a Gaussian function (aperture) given by $$f(p) = \frac{1}{\sqrt{(2\pi)^q |C|}} \exp\left[-\frac{1}{2}(p-p_0)^T C^{-1}(p-p_0)\right] \tag{2}$$

and m(p) is a complex modulating function $$m(p) = \exp[j\omega_0^T(p-p_0)] \tag{3}$$

where $p, p_0, \omega_0 \in R^q$, $C$ is an $q \times q$ positive definite covariance matrix, and $|C| = \det C$.

For the two dimensional (hereinafter "2-D"), the horizontal and vertical spatial coordinates are represented by the vector $p=[x,y]^T$. The shape of the Gaussian function $f(p)$ is controlled by the matrix C, and the vector $p_0=[x_0,y_0]^T$ stands for the translation of its origin. If $\sigma_x$ and $\sigma_y$ are variances of the Gaussian function along the x and y axes respectively, then $$C = \begin{bmatrix} \sigma_x^2 & 0 \\ 0 & \sigma_y^2 \end{bmatrix} \tag{4}$$

where the constants $\sigma_x$ and $\sigma_y$ determine the scale and the width/aspect ratio, which is used to adjust the orientation sensitivity of the Gabor function. The vector $\omega=[u,v]^T$ represents two axial frequencies along two coordinates. The vector $\omega_0=[u_0,v_0]^T$ represents the overall translation frequency of the Gabor function. In two dimensions, the Gabor filter is a 2-D Gaussian envelope, modulating a sinusoid, tuned to the orientation $\theta=\tan^{-1}(v_0/u_0)$ from the u axis, with radial frequency is $(v_0+u_0)^{1/2}$. In the frequency domain, the Gabor function acts as a 2-D bandpass filter represented as a shifted Gaussian, frequency-centered at $\omega_0=[u_0,v_0]^T$. FIG. 1 shows a typical perspective plot of the real component of a Gabor function. In the frequency domain, a Gabor function is a 2-D bandpass filter, represented as a shifted Gaussian function centered at $(u_0,v_0)$:

$$H(\omega) = \exp\left[-\frac{1}{2}(\omega-\omega_0)^T C(\omega-\omega_0)\right]. \tag{5}$$

Equation (1) can be interpreted as the sum of two Gaussian functions that are cosine (real) and sine (imaginary)

modulated. The impulse responses of these odd (real) and even (imaginary) Gabor functions approximate Hilbert pairs. This approximation is more exact when their amplitudes are close, and this can be ensured by choosing a Gabor filter with small half-peak bandwidth.

In the spatial domain, an image is classically described as a collection of pixels, and as a sum of sinusoids of infinite extent in the frequency domain. A fabric image can be represented, wholly or in part, either in the frequency or spatial domain. Both are relevant in a vision system entailing frequency sampling localized in space. The defect segmentation involves identification of regions with uniform textures in a given image. Appropriate measures of texture are required for deciding whether a given region has uniform texture. Defect segmentation in texture requires simultaneous measurements in both the spatial and spatial-frequency domain. Filters with small bandwidths in the frequency domain are more desirable for making fine distinctions among different textures. On the other hand, accurate localization of texture boundaries requires filters that are localized in spatial domain. However, effective width of the filter in the spatial domain and its bandwidth in the frequency domain are inversely related. In this sense, Gabor filters achieve an effective joint resolution in both the spatial and frequency domains.

Accordingly, in an embodiment of the invention, only real Gabor function is used while ignoring corresponding imaginary Gabor function. Real Gabor functions are useful as blob detectors while imaginary Gabor functions can function as proven edge detectors. As previously mentioned, some researchers have shown that odd-symmetric mechanisms (imaginary Gabor function here) are not useful in texture discrimination. While analyzing defects against texture background, we found that the contribution from imaginary Gabor functions is insignificant but they account for nearly 50% of the total computation time. In other words, by approximating the impulse response of real and imaginary Gabor functions as Hilbert pairs we can dispense with the imaginary part of Gabor functions. The analytical form of a 2-D real Gabor function in the spatial domain is given by $$h(x, y)_{mn} = \frac{1}{2\pi |C|^{1/2}} \cos \omega_m^T (p_n - p_0) \exp\left[-\frac{1}{2}(p_n - p_0)^T C^{-1}(p_n - p_0)\right] \quad (6)$$

where m is the index for scale and n is an index for orientation. The spatial modulation frequency $\omega_m$ is only in one direction since we use Gabor function to detect only height and width. The vector $p_0$ shifts the origin of the real Gabor function, so that the output for each input position is shifted by $p_0$. The real Gabor functions for different orientations are obtained by the coordinate transformation $\tilde{p}_n = J_n p_n$ and $\tilde{p}_0 = J_n p_0$, with $$J_n = \begin{bmatrix} \cos\theta_n & -\sin\theta_n \\ \sin\theta_n & \cos\theta_n \end{bmatrix}. \quad (7)$$

The angle $\theta_n$ rotates the real Gabor function for any desired orientation. The parameters $\omega_m$ and $\theta_n$ represent the angular frequency and orientation for the mn channel. The parameters $\sigma_x$ and $\sigma_y$, which define the matrix C, control the bandwidth of the function.

In the illustrated scheme, the power-spectrum of an input image is sampled at different scales and orientations. The complete set of self-similar Gabor functions used to sample the input image is obtained by rotation (varying $\theta_n$) and scaling (varying $\omega_m$) of the basic Gabor function. Sixteen example Gabor filters that sample the input image in the Fourier domain in a log-polar scheme at four orientations and four scales are shown in FIG. 2. The circles in FIG. 2 represent the bandwidth of the corresponding Gabor filters at half-peak magnitude. Four spatial frequencies ($f_{max}$, $f_{max}/2$, $f_{max}/4$, $f_{max}/8$) shown in FIG. 2 are distributed in octaves, each of which is further rotated in steps of 45° (0°, 45°, 90°, 135°). Thus, a bank of real Gabor functions corresponding to the 16 channels shown in FIG. 2 capture features from the input image. In an embodiment of the invention, as a compromise between computational load and performance, the total number of channels is limited to 16. Interestingly, there is psychophysical evidence that the human visual system uses a similar number of channels. For an input image i(x,y) and a real Gabor function $h(x,y)_{mn}$ of size N×N, the filtered image $I_{mn}(x,y)$ is obtained as $$I_{mn}(x, y) = h(x, y)_{mn} * i(x, y) \quad (8)$$

$$= \sum_{k=1}^{N} \sum_{l=1}^{N} h_{mn}(k, l) i(x - k, y - l).$$

where '*' denotes the convolution operation. The above operation requires half the computational time for the calculation of feature vectors as compared to the case in which complex Gabor functions are used.

An appropriate filter design with small convolution masks allows an efficient implementation of real Gabor functions in the spatial domain. The size of this real-Gabor-function mask determines, in part, the computational efficiency with tradeoffs. For instance, reliable measurements of texture features call for large mask sizes. On the other hand, large mask size significantly increases the computational load that is undesirable for online inspection. This follows from the total number of real operations (additions and multiplications) for each of the sixteen channels being proportional to $N^2$, where N×N is the filter mask size (or simply the mask parameter). An embodiment of the invention employed with little degradation in performance 7×7 filter masks instead of 9×9 filter masks to achieve about 40% saving of computational load per frame. Similarly, with some marginal and acceptable degradation in performance, another embodiment of the invention employed 5×5 filter masks resulting in about 70% saving (as compared with 9×9 masks) of computational load per frame. Preferably, 5×5 filter mask, even more preferably a 9×9 filter mask and most preferably a 7×7 filter mask is used in most embodiments of the invention. However, these preferences are not intended to limitations on the scope of the invention.

The performance of this algorithm as a function of mask size for various defects is discussed later. For obtaining the values with a particular mask, every image pixel of fabric under inspection is convolved with the real Gabor function mask (equation (6)) to obtain the filtered pixel value. This operation provides a set of 16 images from each of the sixteen channels for use as a feature vector for defect segmentation.

In order to identify defects against a textured background, it is necessary to select a set of suitable channel filters. Gabor filters, acting as bandpass filters, with appropriate parameter choices, can be tuned to discriminate local fabric defects. Accordingly, in an embodiment of the invention, the choice of particular filters is described in greater detail next.

FIG. 1 illustrates real Gabor functions having a spatial modulation frequency so as to produce one large positive lobe and two smaller negative lobes on either side. Such Gabor filters function as blob detectors. The illustrated filters exhibit circular symmetry ($\sigma_x=\sigma_y=\sigma$) and a spatial bandwidth proportional to spatial frequency. For Gabor filter defined by equation (1), the half-peak magnitude axial ($B_a$) and orientation bandwidths ($B_\theta$), shown in FIG. 3, are defined as $$B_a = \log_2\left(\frac{\omega_m\sigma + \sqrt{2\ln2}}{\omega_m\sigma - \sqrt{2\ln2}}\right), \quad B_\theta = 2\tan^{-1}\left(\frac{\sqrt{2\ln2}}{\omega_m\sigma}\right) \quad (9)$$

$$B_a = \log_2\left(\frac{\omega_m\sigma + \sqrt{2\ln2}}{\omega_m\sigma - \sqrt{2\ln2}}\right), \quad B_\theta = 2\tan^{-1}\left(\frac{\sqrt{2\ln2}}{\omega_m\sigma}\right)$$

Interestingly, experiments show that frequency bandwidth of cells in visual cortex is about one octave. This is in accord with the choice for fixing axial bandwidth as one octave. Equation (9) shows that this can be achieved by setting $$\sigma = \frac{3\sqrt{2\ln2}}{\omega_m} \quad (10)$$

Thus, radial and angular bandwidths are constant on log-polar scale at one octave and 36.87° respectively. The spatial frequency plane of acquired fabric image is divided into four different orientations (0°, 45°, 90° and 135°). A common method of decomposing the frequency band, motivated by human vision model, has been to use octave band (dyadic) decomposition. Therefore, the radial axis of spatial frequency plane is divided into four equal octave bands (centered at $f_1, f_2, f_3$, and $f_4$). As is known, in a bandwidth of one octave, spatial frequency increases by a factor of two. The highest central frequency for each direction is located at Nyquist frequency to avoid ringing and noise. The resultant filter bank performs log-polar sampling of acquired fabric image.

The width of the thinnest yarn of this fabric, expressed in terms of number of pixels, determines the maximum frequency of interest. Let $f_1$ be this maximum frequency, also denoted by $f_{max}$. This choice of radial frequency guarantees that the passband of the filter with highest radial frequency (i.e. $f_{max}$) falls inside the image array. Thus the next radial frequency of the Gabor filter, $f_2$ is selected at the next lower octave channel (one octave away), i.e. $f_2=f_{max}/2$. Similarly, $f_m=f_{max}2^{1-m}$ (m=1, 2, 3, 4). For a particular fabric, if the thinnest yarn occupies 12 pixels, then $f_{max}=\frac{1}{12}$ cycle/pixel. With a maximum frequency of this order, few defects whose sizes are approximately that of one yarn are expected to be detected. The larger defects can be located with filters of lower frequencies. That is, the greater is the extent of the defect, the lower is the filter frequency required for its detection. The contour location of sixteen example Gabor filters along with their respective center frequencies is shown in FIG. 2. FIG. 4 illustrates the sixteen real Gabor functions in the spatial domain.

In an other aspect, an embodiment of the invention enables automated selection of the central frequency, thus, reducing the need for manual tuning. The selection of $f_{max}$ requires calibration whenever the fabric type (texture) or image acquisition conditions are varied. This calibration is proportional to the width of thinnest yarn in the fabric, which is a function of frequency-domain parameters. Therefore, the spectral analysis on a defect-free (reference) fabric image allows automatic selection of the magnitude of $f_{max}$. Due to the nature of fabric structure, the dominant spectral peaks lies along the two axes of the frequency spectrum.

From a defect-free fabric image $i_r(x,y)$, a vector consisting of complete row of pixels $i_r(y)$ (preferably from the center of image) is selected for spectral analysis since experimental results show that the location of vector $i_r(y)$ (position of x) has little effect on the desired magnitude of $f_{max}$. Then signal $i_r(y)$ is adjusted to have a zero mean by removing the mean value.

$$i'_r(y) = i_r(y) - \frac{1}{Q}\sum_{y=0}^{Q-1} i_r(y) \quad (11)$$

where the size of reference image $i_r(x,y)$ is P×Q pixels. This signal $i_r'(y)$ is converted to frequency domain by taking the discrete Fourier transform of signal $i_r(y)$ using a 512-point fast Fourier transform (FFT).

$$I_r(k) = \sum_{y=0}^{N-1} i'_r(y)G_Q^{yk} \text{ for } k = 0, 1, 2, \ldots, Q-1. \quad (12)$$

where Q is the length of vector $i_r(y)$, and $G_Q = e^{-j2\pi/Q}$. From $I_r(k)$, the power spectral density (PSD) of signal $i_r'(y)$ is computed as follows:

$$P(k)=I_r(k)I_r(k)^*/Q \quad (13)$$

where $I_r(k)^*$ is the complex conjugate of $I_r(k)$. The power distribution in P(k) reflects the frequency components associated with the main background texture of the defect-free image. The normalized frequency at which the peak of power spectral density P(k) occurs can be chosen as $f_{max}$. The selection of $f_{max}$ for a typical fabric sample used in this work is shown in FIG. 5.

The above-described method computes $f_{max}$ from the horizontal row of pixels along the warp direction, i.e. $i_r(y)$. Since the yarn density (warp×weft, per inch) of the reference image used is known in advance, and therefore (warp>weft) the row of pixels only from the warp direction is used. This choice is also supported by experiments, i.e. the magnitude of $f_{max}$ computed from a column of pixels $i_r(x)$ was found to be smaller than when it is computed from a row of pixels $i_r(y)$. However, in situations where the yarn density of the fabric is not known, the magnitude of $f_{max}$ is computed from both, i.e. $i_r(x)$ and $i_r(y)$, and the highest of $f_{max}$ from these two magnitudes is used. A rather accurate but computationally expensive method utilizes 2-D power spectral density of the defect-free reference image to compute the magnitude of $f_{max}$. However, the accurate selection of $f_{max}$ is not critical and the approximate method presented in this invention computes $f_{max}$, which serves as a good measure of the highest frequency of interest.

Figure 8A:
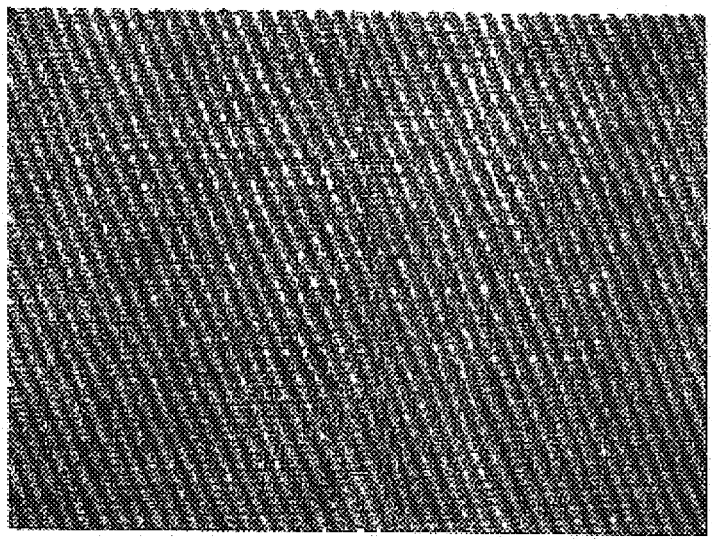
Figure 8B:
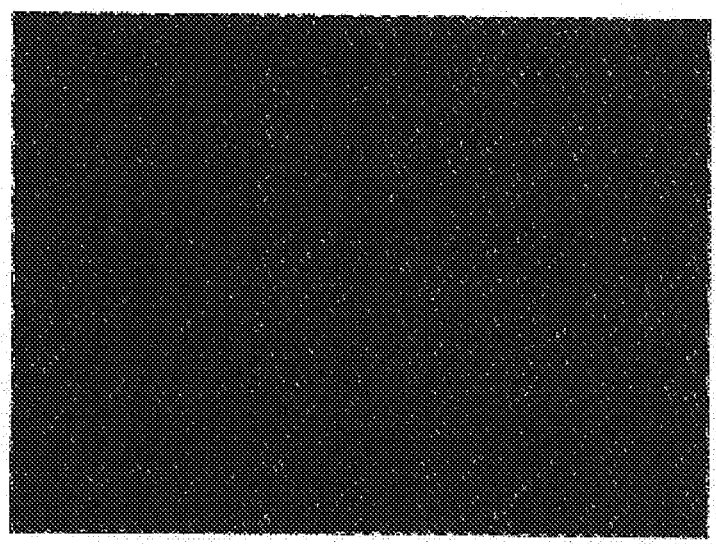
Figure 8C:
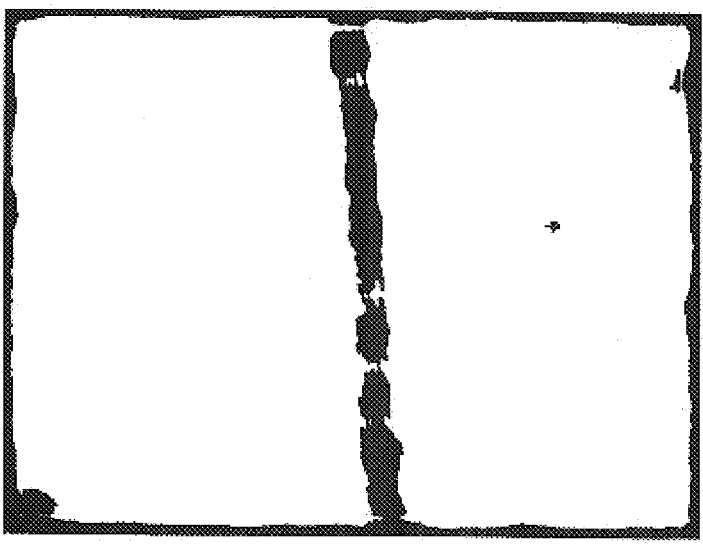
Figure 9A:
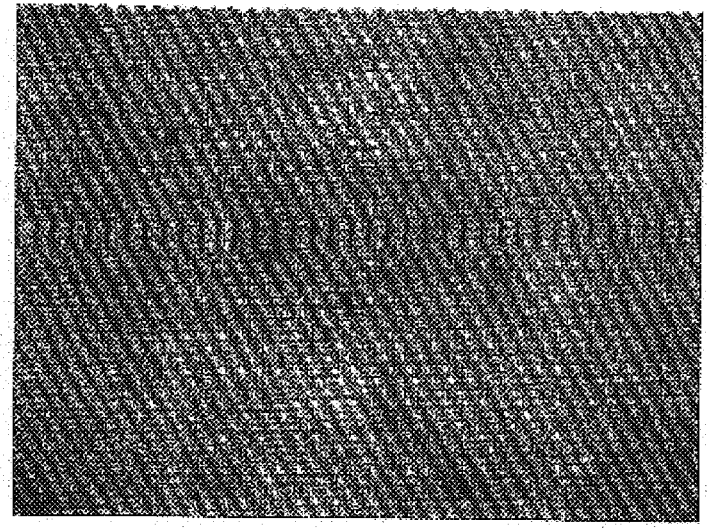
Figure 9B:
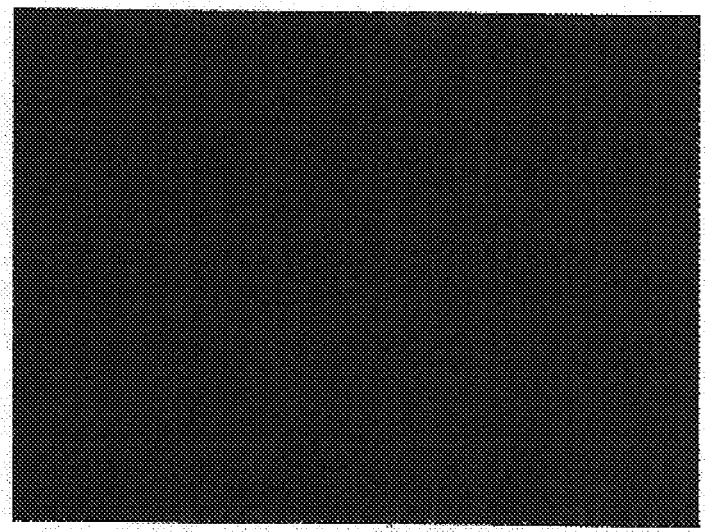
Figure 9C:
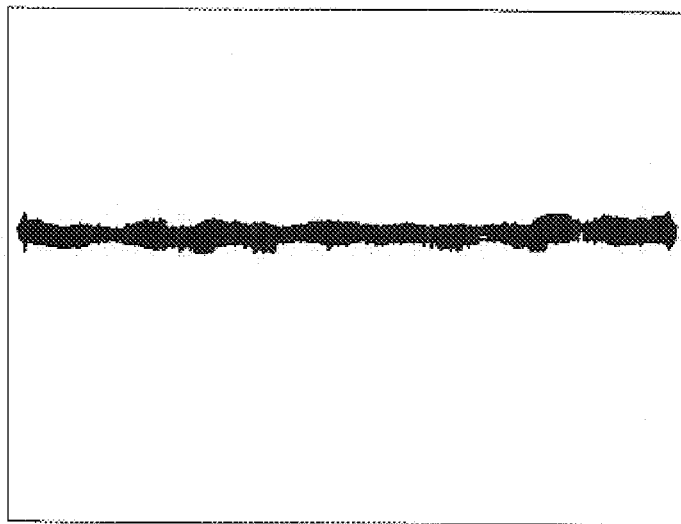

If a priori knowledge regarding the orientation and size of local fabric defect is made available, it can be regarded as supervised defect segmentation. In such cases, segmentation can be performed using just one (or few) appropriately tuned Gabor filter instead of bank of Gabor filters. FIG. 8 clearly depicts successful supervised defect segmentation using a Gabor filter. From the visual examination of fabric sample in FIG. 8(A) it can be observed that the defect is approximately one yarn wide and is located at about 90° in spatial plane. Since one yarn in this image occupies 24 pixels (approximately), therefore a Gabor filter located at $f=\frac{1}{24}$ cycle/pixel is chosen. A 15×15 Gabor filter mask with $f=\frac{1}{24}$, $\theta=90°$, and half-peak bandwidth of one octave [equation (10)] was found to be appropriate for attenuation of background and accentuation of defects. Further a 9×9 median filter suppresses the specle-like noise from the filtered image and the resulting image of FIG. 8(B) was thresholded to obtain binary image of segmented defect shown in FIG. 8(C). The thresholding value is obtained from equation (18). The median filtering attenuates irrelevant spectral features that do not contribute to an efficient segmentation using thresholding operation. FIG. 9(A) shows another fabric sample in which observed defect is approximately 2 yarns wide and is oriented at 90° in the spatial plane. A similar processing of this image yields the image in FIG. 9(B) followed by segmented defect shown in FIG. 9(C). For the fabric sample images shown in FIGS. 8–9, defect segmentation can also be achieved with convolution mask smaller than 15×15 however with some degradation in performance as the segmented defect is not clear as shown in results in FIGS. 8–9.

A supervised approach naturally has additional limitations as compared to the flexibility of unsupervised approach. However, in many industrial inspection applications it can be assumed that the orientation and resolution of defects are fixed. Supervised defect segmentation then can be economically implemented on general-purpose hardware for inspection of defects of known sizes in a known direction. However, unsupervised defect segmentation is a more critical task and is more suitable for automated visual inspection of local defects in industrial web materials. This approach is detailed next.

In another aspect, an embodiment of the invention enables integration of images corresponding to different filters. A desirable fabric defect detection system integrates defects captured at different orientations and resolution levels of Gabor filter. The desired output is a binary image of local defects in the fabric. A desired robust, automatic and flexible procedure for fabrics with different structures is described in an embodiment of the invention.

Before the system is ready for on-line inspection a defect free sample of fabric is required to compute off-line parameters. Vibration free images of the fabric under test are acquired using backlighting in step 600 of FIG. 6 followed by geometric correction for lighting artifacts during step 605. As shown in FIG. 6, three offline parameters are pre-computed from reference samples during steps 610, 615, and 620 to obtain frequency $f_{max}$, the mean and standard deviations from each of the 16 blob descriptors ($R_1$ to $R_{16}$) and, the thresholding limit respectively. An example block diagram for online inspection procedure is shown in FIG. 7.

The block diagram for online inspection system of FIG. 7 starts T step 700 with acquisition of image of fabric i(x,y) to be inspected for defects. The acquired images exhibited artifacts of brightness gradient due to non-homogenous lighting. These artifacts are corrected during step 705 by subtracting acquired images with a reference image. This reference image of plain white paper was acquired under the same illumination condition. The set of real Gabor functions are applied to this corrected image to obtain the set of 16 filtered images ($F_1$ to $F_{16}$) during step 710. A non-linear operator on these images ($F_1$ to $F_{16}$) generates corresponding blob descriptors ($T_1$ to $T_{16}$) during step 715. A similar set of operations on a defect-free fabric sample (reference) generates blob descriptors ($R_1$ to $R_{16}$) for a reference fabric sample. As shown in FIG. 7, the mean and standard deviations from each of the sixteen blob descriptors ($R_1$ to $R_{16}$) are computed at the beginning and stored before the beginning of the fabric inspection (offline) during step 720. This set of mean and standard deviations are utilized to generate feature difference array ($TDD_1, \ldots, TDD_{16}$) during step 725. Sensitivity control 735 enables monitoring of noise along with generation of sixteen images ($S_1$ to $S_{16}$) during step 730. As shown in FIG. 7, these images ($S_1$ to $S_{16}$) are subjected to image fusion and a set of four images ($N_1$ to $N_4$) corresponding to each of the four scales (m) is obtained during step 740. These images ($N_1$ to $N_4$) are combined during steps 745 and 750 to a single image output N so as to further reduce false alarms. This image N is subjected to calibration during step 755 (described later) and the result in step 760 is a final image of segmented defects (if any) in the fabric sample under inspection.

For reliable defect segmentation, it is necessary to have a set of feature vectors that can characterize the texture. These texture features form the basis for defect segmentation. A transform/function for enhancing the changes in each of 16 images ($F_1$ to $F_{16}$), possibly corresponding to a defect, in such a way that a thresholding operation can segment the defect from the textured background is described next.

As noted previously, the energy distribution in frequency domain identifies a texture or a defect. Based on this assumption, a local energy function calculates texture blob descriptors. The objective of the local energy function is to estimate the energy in the sixteen filtered images in the local region, preferably with the aid of non-linear local energy functions to enhance computational efficiency. Some well-known non-linear functions are magnitude |x|, squaring |x|, and the rectified sigmoid |tan h βx|. The rectified sigmoid is an important non-linear function similar to sigmoidal activation function commonly used in artificial neural networks. In contrast to rectified sigmoid, magnitude and squaring non-linear functions do not require any tuning parameters. However, such a parameter is an advantage in many situations because the parameter β can be tuned. Therefore, this local energy function is appropriate for our application. Accordingly, $T_1$ is obtained as $$T_1(x,y)=|f[F_1(x,y)]|, \ f(t)=\tan h(\beta t). \tag{14}$$

Similarly, a new set of sixteen images, described here as texture blob descriptors ($T_1$ to $T_{16}$) are obtained. The parameter β, which gives saturation characteristics of this function, depends on the dynamic range of gray levels in the acquired images. Empirically, this is fixed at 0.3 to give fast saturating, threshold-like function. The application of local energy function transforms the sinusoidal modulations in the filtered image to square modulations. Therefore, this operation can be interpreted as blob detector. Since non-linear function used for each of sixteen the filtered image ($F_1$ to $F_{16}$) is odd-symmetric, the texture blob descriptors ($T_1$ to $T_{16}$) are accompanied by both dark and light blobs.

Individual blobs in ($T_1$ to $T_{16}$) are identified and their attribute to defect or defect-free texture is assigned. Texture descriptors for the reference or defect-free fabric sample ($R_1$ to $R_{16}$) are also obtained in a similar manner. For each of these sixteen texture descriptors corresponding to the defect free sample, we obtain the mean and standard deviation, e.g., step 725 of FIG. 7. This set of means and standard deviations is used for further characterization of each pixel from the texture blob descriptors ($T_1$ to $T_{16}$), e.g., steps 725 and 730 of FIG. 7.

Texture features characterized by enhanced local gray-level statistical distribution [equation (14)] are asymptotically uniform for defect-free fabric (in sufficiently large image areas). Given a prototype of fabric under test, defect segmentation requires identification of proper distance among such distributions. Classical approaches based on estimation of some statistical moments (e.g. mean value, standard deviation, etc.) or other statistical parameters allow a very quick characterization of image pixels. On the other hand, methods based on higher-order statistics (e.g. co-occurrence matrix, run-length metrics and statistical feature matrices) provide more information but are highly demanding in terms of both computational and memory requirements. Furthermore, processing texture blob descriptors $T_1$ to $T_{16}$ by using first order statistical analysis avoids a possible computational bottleneck in the online fabric defect detection system.

The set of texture blob descriptors ($T_1$ to $T_{16}$) forms the basis for defect segmentation. From these descriptors, a comparison for each pixel of defective fabric with that of defect free fabric is made. If the difference is small, probability of a pixel corresponding to the defect-free sample is high. Alternatively, when the difference is large, it is highly probable that this pixel corresponds to a defect. For each of the texture blob descriptors, texture descriptor difference (magnitude) TDD can be written as:

$$TDD(x,y) = |T(x,y) - m_{defect-free}| \quad (15)$$

where $m_{defect-free}$ is the mean of corresponding texture blob descriptor for defect free fabric ($R_1$ to $R_{16}$). Next, the standard thresholding operation to reduce the noise is performed, e.g., step 730 of FIG. 7. For each of the pixels in TDD, we find corresponding pixel in S:

$$S(x,y) = \begin{cases} TDD(x,y) & \text{if } TDD(x,y) \geq \tau \cdot sd \\ 0 & \text{Otherwise.} \end{cases} \quad (16)$$

The thresholding is thus proportional to the standard deviation (sd). This standard deviation is calculated from each of its sixteen texture blob descriptors of defect free fabric, i.e. $R_1$ to $R_{16}$. The magnitude of the coefficient $\tau$ depends on the sensitivity as fixed by the user. The motivation behind the introduction of 'sensitivity control' in our algorithm is twofold. When we increase the size of image per frame in an attempt to increase the performance, the mean gray level variation in the resulting image tends to be uniform. Now the thresholding limit has to be much smaller (highly sensitive) to discriminate the defective pixels. We have found that a thresholding limit equal to one standard deviation increases the sensitivity and is most suitable for large area images with uniform mean gray level. Secondly, when the image size per frame is small so that gray level variations are considerably non-uniform, a thresholding limit of twice the standard deviation (medium sensitivity) is appropriate. On the other hand, when the number of yarn impurities in the fabric is high, the sensitivity has to be kept low (thrice of standard deviation) to discriminate the defects against the noisy background. Thus the sensitivity control largely depends on fabric texture and image acquisition conditions, and must be adjusted accordingly.

Evaluating the reliability of texture difference pixels from different channels is helpful when the texture difference images reveal inconsistencies. A number of fusion algorithms have been developed in the literature and used to reduce false alarm while maintaining high probability of detection. One approach for target detection involves deliberate generation of unwanted output (clutter) followed by its subtraction from detection output. Binary fusion algorithm uses logic AND of outputs obtained from several detection outputs. However binary fusion algorithm does not weigh different confidence level in different detection outputs. Not surprisingly, analog and hierarchical fusion algorithms have produced better results i.e. lower false alarm rate. Analog and hierarchical fusion algorithm uses a mapping function to convert different detection outputs into a common range. This step, similar to the fuzzification function used in fuzzy logic, is also used in a fusion algorithm based on Bernoulli's rule of combination, however with different membership function.

The main function of image fusion module in an embodiment of the invention is to attenuate background pixels and accentuate defective pixels from four directions. Bernoulli's rule of combination, which is special case of Dampster's rule of combination, is extended here for integrating images from four directions. For each of the four images in every scale m, following mapping function converts pixel values into a common output range of 0–1.

$$O_{mn}(x,y) = \frac{S_{mn}(x,y) - \min[S_{mn}(x,y)]}{\max[S_{mn}(x,y)] - \min[S_{mn}(x,y)]} \quad (17)$$

where the image input $S_{mn}(x,y)$ in equation (17) is same as $S(x,y)$ from equation (16), but has been subscripted with index for scale m and orientation n [equation (6)]. Thus for equation (17) the feature difference images $S_1$ to $S_4$ are denoted by $S_{11}(x,y)$ to $S_{14}(x,y)$ to illustrate that the images have originated from real Gabor functions at scale m=1 and orientation n=1, 2, 3, 4 (0°, 45°, 90°, and 135°). Next, a fused output $N_m(x,y)$ is generated for every scale m, by fusion of normalized images [equation (17)] from four directions, e.g., during step 740 of FIG. 7.

$$N_m(x,y) = \sum_{n=1}^{4} O_{mn}(x,y) - \begin{cases} O_{m1}(x,y)O_{m2}(x,y) + O_{m2}(x,y)O_{m3}(x,y) + O_{m3}(x,y)O_{m4}(x,y) + \\ O_{m4}(x,y)O_{m1}(x,y) + O_{m4}(x,y)O_{m2}(x,y) + O_{m3}(x,y)O_{m1}(x,y) \end{cases} \quad (18)$$

Thus, for every scale m=1, 2, 3, 4, we obtain one fused image output $N_m(x,y)$ from the four images $S_{m1}(x,y)$, $S_{m2}(x,y)$, $S_{m3}(x,y)$ and $S_{m4}(x,y)$ using (17) and (18). These fused outputs tend to follow one of the inputs closely, if the other inputs possess low values. On the other hand, the input with very high values tends to dominate the outputs, regardless of the values of the other inputs. Thus, the pixels from the defects captured in any of the four orientations will dominate in the final fused image for each scale and the fusion suppresses the noise and combines sixteen images ($S_1$ to $S_{16}$) into four images ($N_1$ to $N_4$).

Due consideration to reduce false alarm should be given when the information gathered from four different resolution levels ($N_1$ to $N_4$) is combined. It is reasonable to assume that a defect will appear in at least two adjacent resolution levels, otherwise it is highly unlikely that it is a defect. This consideration has been found to reduce false alarms without affecting defect identification e.g., during step 745 of FIG. 7. This is ensured by computing geometric means of every adjacent level in an embodiment of the invention. For example, $N_{12}$ is computed as $$N_{12}(x,y) = [N_1(x,y)N_2(x,y)]^{1/2} \quad (19)$$

Next, a set of three images $N_{12}$, $N_{23}$, and $N_{34}$ are obtained. An arithmetic mean combines defects captured by them e.g., during step 750 of FIG. 7. Notably, this image N(x,y) contains contribution from all sixteen texture descriptors ($T_1$ to $T_{16}$):

$$N(x, y) = \frac{1}{3}[N_{12}(x, y) + N_{23}(x, y) + N_{34}(x, y)]. \quad (20)$$

Finally, the image is subjected to thresholding based on a calibrated value e.g., during step 755 of FIG. 7. A thresholding value is selected such that values below this limit are considered as belonging to regular texture in the fabric, and values above are contributed from the defects. Advantageously, this value is suitably obtained by calibration of the system at the beginning of the operation using a fabric sample without any defects and yarn impurities. With the use of this reference image, the $N_{defect-free}(x,y)$ is obtained from equation (20). The threshold value $\eta_{th}$ is obtained by:

$$\eta_{th} = \max_{x,y \in W} \{N_{defect-free}(x, y)\}. \quad (21)$$

where 'W' is a window centered at the image. Thus the threshold value $\eta_{th}$ is the maximum amplitude of gray levels, within a window 'W', in the image $N_{defect-free}(x,y)$ obtained from the reference image. The choice of the window size avoids the effect from border distortion. This is obtained by removing ten pixels (ad hoc) from each side of the image $N_{defect-free}(x,y)$. This window size depends on the mask size of real Gabor functions; as for 7×7 mask, at least seven pixels from the border have to be ignored. The magnitude of $\eta_{th}$ is such that isolated noisy pixels in $N(x,y)$ are isolated in the output binary image. Binarization based on this threshold limit suppresses noise, although this operation also suppresses some of the defects captured at different orientations and frequencies.

Another, less preferred, approach for computing the threshold value is based on the mean and standard deviation of final image ($N_{defect-free}(x,y)$ here). Experimental results show that this threshold value generates large noise in the output and requires opening operation with a convolution mask (typically 3×3) to eliminate the noise. With the usage of threshold value suggested in equation (21) opening operation is not needed and this results in reduction of computational load, which is critical for real time implementation of this algorithm.

This defect segmentation algorithm has been tested on both synthetic and real test fabric images. The reason for testing this algorithm on synthetic images was to ensure that the algorithm is able to discriminate difficult fabric defects, which humans can discriminate preattentively. The image acquisition subsystem developed at the Industrial Automation Laboratory at the University of Hong Kong has been used to capture gray level images of defective test fabrics. All non-synthetic images during testing were acquired using back lighting. Samples of the most commonly occurring fabric defects (e.g. mixed filling, waste, mispicks, kinky filling, misreed etc.) were gathered from a loom and their gray level images were used to evaluate the algorithm described. Some example results are presented here.

FIGS. 11(A) and (B) show synthetic binary images of test and reference fabric respectively. The second row of the test image has two more pixels than other rows. This simulated defect of thick yarn can be seen segmented in the final image in FIG. 11(C). FIGS. 10(A) and (B) show the real fabric images, with defect segmented in FIG. 10(C). The border effect in the segmented image is localized and the border distortion can be ignored.

An accurate segmentation of defect is limited by the rather poor yarn quality. Impurities that are naturally present in fabric yarns tend to obscure more subtle defects. This effect can be seen in FIG. 12. The fabric image A in FIG. 12 has defects along with large yarn impurities. The defects are segmented at three different sensitivities namely low (B), medium (C) and high (D) as shown in FIG. 12. As seen from results in FIG. 12, low sensitivity (B) helps to suppress the yarn impurities but at the expense of some pixels from the defect. However, while segmenting defect from fabric with large impurities, sensitivity is reduced to avoid yarn impurities appearing as defect in output.

Figure 20A:
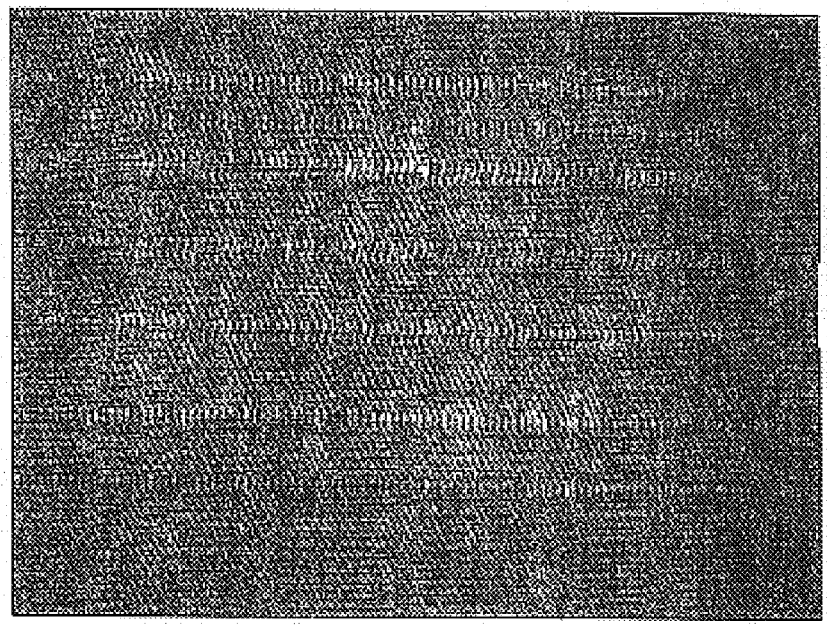
Figure 20B:
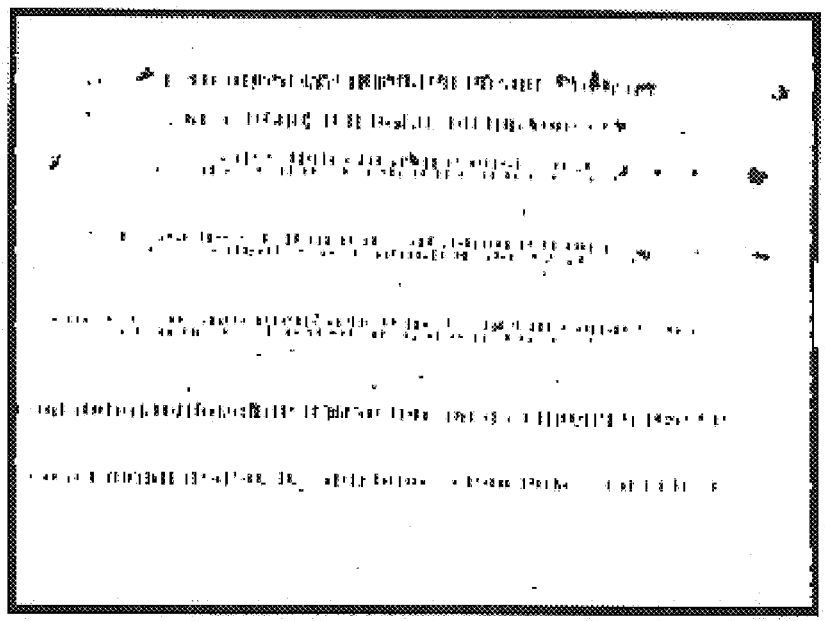

The image acquisition sub-system was adjusted to acquire large size images while fabric is in motion with the velocity of 30 cm/sec. The acquired images were digitized in 385×287 pixels, with eight-bit resolution (256 gray levels). Nine images of fabric with defects were chosen to have large characteristic variability in terms of composition and structure. It is assumed that these sample images are representative of fabric defects in textile industry. All these images covered a 10 cm width and 7.5 cm height of actual fabric. FIGS. 13–21 illustrate the defect segmentation achieved with the proposed algorithm. Due to the increase in the area of fabric per frame, we have increased the sensitivity ($\tau=2$). FIG. 20(A) shows fabric sample, with defects in which are visible only with difficulty. The defects appear only alter the spatial arrangement of neighboring pixels instead of mean gray level. Real Gabor functions register this change with enhanced discrimination enabled by the choice of the local energy function resulting in successful segmentation as shown in FIG. 20(B).

TABLE 1

| Mask Size | L | M | H | L | M | H | L | M | H |
|---|---|---|---|---|---|---|---|---|---|
| | Sample 13(A) | | | Sample 14(A) | | | Sample 15(A) | | |
| 5 × 5 | 5.98 | 42.11 | 39.66 | 0.23 | 0.10 | 0.14 | 0.02 | 0.03 | 0.04 |
| 7 × 7 | 0.61 | 34.92 | 37.83 | 0.33 | 0.14 | 0.28 | 0.00 | 0.22 | 0.05 |
| 9 × 9 | 2.30 | 14.40 | 30.02 | 0.42 | 1.63 | 0.70 | 0.00 | 0.03 | 0.02 |
| | Sample 16(A) | | | Sample 17(A) | | | Sample 18(A) | | |
| 5 × 5 | 0.01 | 0.43 | 2.80 | 0.13 | 0.29 | 0.21 | 1.89 | 3.92 | 4.28 |
| 7 × 7 | 0.04 | 0.17 | 2.57 | 0.06 | 0.84 | 0.25 | 1.60 | 1.67 | 2.69 |
| 9 × 9 | 0.03 | 0.08 | 0.75 | 0.13 | 0.33 | 0.04 | 1.02 | 1.81 | 3.34 |
| | Sample 19(A) | | | Sample 20(A) | | | Sample 21(A) | | |
| 5 × 5 | 0.68 | 1.28 | 2.14 | 0.10 | 1.76 | 1.79 | 2.58 | 5.30 | 5.69 |
| 7 × 7 | 0.08 | 0.53 | 3.42 | 0.11 | 0.76 | 9.34 | 1.07 | 1.41 | 3.13 |
| 9 × 9 | 0.96 | 0.56 | 3.81 | 0.01 | 0.19 | 4.87 | 0.40 | 1.58 | 3.63 |

Percentage of Misclassified Defective Pixels

The lack of appropriate quantitative measures for the goodness of segmentation makes it difficult to evaluate and compare different defect detection methods. A simple criterion that has been used in many texture segmentation algorithms is the percentage of misclassified pixels. In defect segmentation problem, defective pixels are of interest and therefore percentage of total defective pixels misclassified are reported in TABLE 1 for several samples at different levels of sensitivity ranging from low ("L") to medium ("M"), to high ("H"). The sample numbers in TABLE 1 correspond to the figures. Thus, e.g., sample 19(A) is depicted in FIG. 19(A).

Figure 14B:
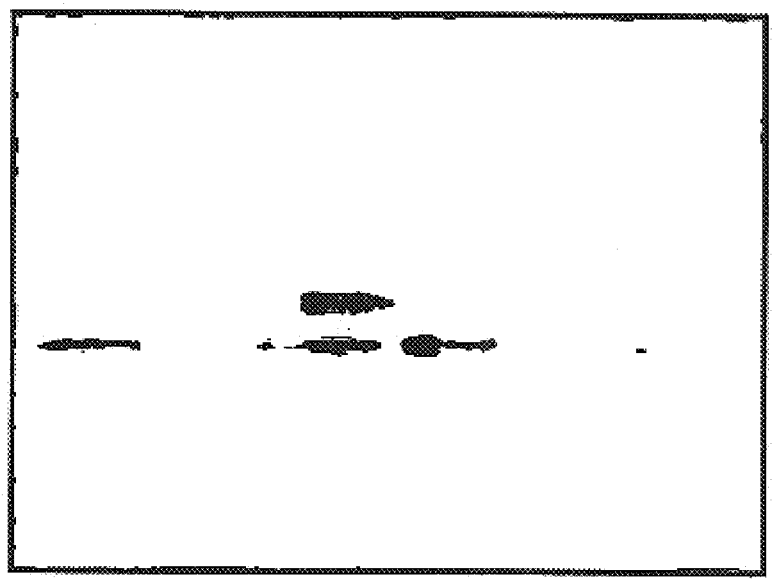

In TABLE 1 as sensitivity increases from low to high, the percentage of misclassified pixels increases for every image sample (for 7×7 mask). However sample in FIG. 14(B) is an exception. Another effect on performance due to with the variation in mask size can be observed. At the medium sensitivity, indicated by the heading "M" in TABLE 1, as the mask size is increased from 5×5 to 9×9, there is a decrease in percentage of misclassified pixels for every image sample with the exception of the samples in FIGS. 14(B) and 17(B).

Figure 17B:
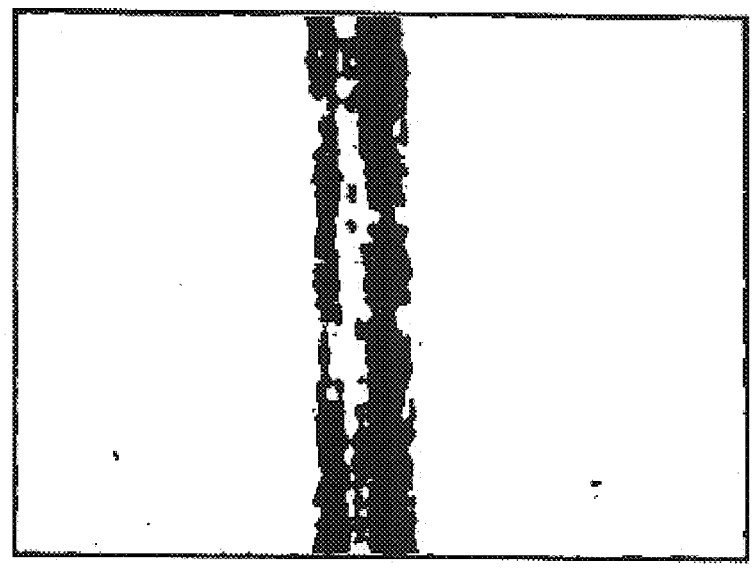

In TABLE 1 image sample from FIG. 17(B) registered highest increase in performance (9.26 times) with the increase in mask size from 5×5 to 9×9 at the medium sensitivity. For the image samples shown in FIGS. 13–21 the percentage of misclassified pixels is below 2%, however one sample in FIG. 13(B) provides an exception. A conclusion drawn from TABLE 1 is that there is an overall reduction in percentage of pixels misclassified as defects, with increase in mask size and decrease in sensitivity. FIG. 22 shows the percentage of pixels occupied by fabric defects in an acquired image plotted against percentage of misclassified pixels from the defect. This plot illustrates a general decrease in false alarms with increase in defect per frame.

The criterion used in TABLE 1, percentage of misclassified pixels, does not accurately reflect the ability of the algorithm to segment the defect. Low percentage of misclassified pixels does not necessarily mean good defect segmentation, unless a large number of pixels showing defect in defective region accompany it. Therefore, some of the results from TABLE 1 are elaborated in TABLES 2, 3, and 4.

TABLE 2

| Total | 5 × 5 | | | 7 × 7 | | | 9 × 9 | | |
|---|---|---|---|---|---|---|---|---|---|
| Pixels | L | M | H | L | M | H | L | M | H |
| P1 | 44 | 100 | 92 | 61 | 124 | 104 | 66 | 104 | 93 |
| P2 | 653 | 653 | 653 | 653 | 653 | 653 | 653 | 653 | 653 |
| P3 | 39 | 275 | 259 | 4 | 228 | 247 | 15 | 94 | 196 |

Figure 13A:
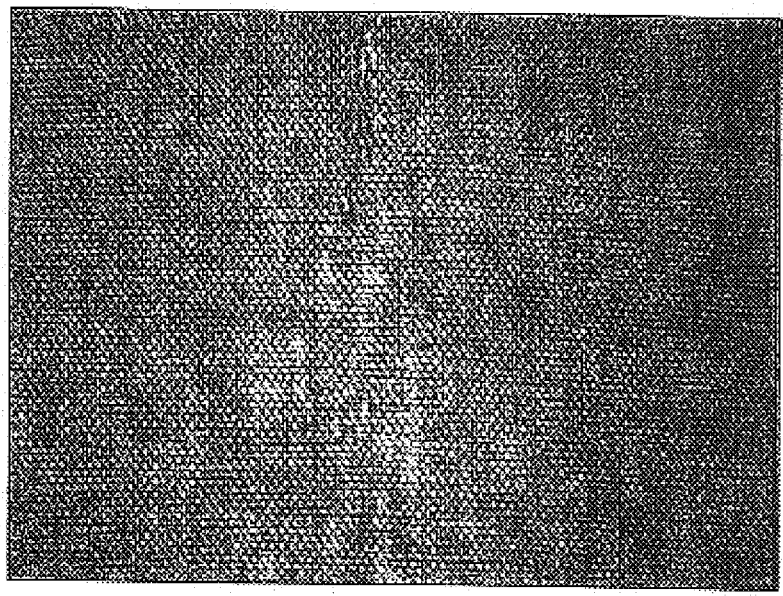
Figure 13B:
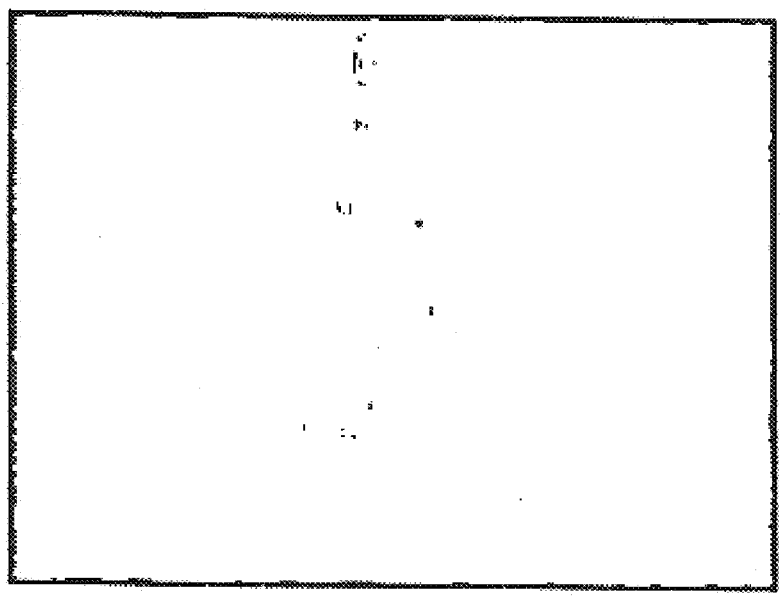

Performance Analysis for the Sample Shown in
FIG. 13(A)

TABLE 3

| Total | 5 × 5 | | | 7 × 7 | | | 9 × 9 | | |
|---|---|---|---|---|---|---|---|---|---|
| Pixels | L | M | H | L | M | H | L | M | H |
| P1 | 5890 | 9780 | 11629 | 5442 | 9675 | 12811 | 5362 | 8541 | 12649 |
| P2 | 23609 | 23609 | 23609 | 23609 | 23609 | 23609 | 23609 | 23609 | 23609 |
| P3 | 2 | 101 | 660 | 10 | 39 | 607 | 7 | 18 | 177 |

Performance Analysis for the Sample Shown in
FIG. 16(A)

TABLE 4

| Total | 5 × 5 | | | 7 × 7 | | | 9 × 9 | | |
|---|---|---|---|---|---|---|---|---|---|
| Pixels | L | M | H | L | M | H | L | M | H |
| P1 | 4898 | 16987 | 19660 | 3822 | 15934 | 22548 | 2167 | 10001 | 17952 |
| P2 | 40957 | 40957 | 40957 | 40957 | 40957 | 40957 | 40957 | 40957 | 40957 |
| P3 | 28 | 526 | 876 | 32 | 216 | 1402 | 21 | 56 | 1684 |

Performance Analysis for the Sample shown in
FIG. 19(A)

In the examples summarized in TABLES 1–4 above, P1: Defective pixels identified; P2: Actual defective pixels (obtained by visual examination); P3: Noise, pixels appearing as defects in defect free region, sensitivity: L (low), M (medium), H (high) and the total number of pixels in image window is 97,455. As seen in TABLES 2–4, the increase in sensitivity results in a general increase in defective pixels (P1). However, this is accompanied by an increase in pixels appearing outside the defective region (P3) i.e. noise. With increase in mask size, output defective pixels (P1) also increase. But, this small increase often requires about 50(70)% more computation when mask size is increased from 5×5 to 7×7 (9×9). Thus, in view of these experimental results, the 7×7 mask is well suited for many applications without any significant deleterious change in output. Similarly, 5×5 masks can be used with a marginal compromise in the output corresponding to smaller sized defects.

This invention provides improvements in by two considerations—computational complexity and performance. For adequate real time performance, a successful algorithm reduces computational complexity without compromising performance. Accordingly, the taught combined feature vectors described herein reduce the probability of false alarm while maintaining high probability of detection.

It is well known in the textile industry that the majority of weaving defects occur either in the direction of motion (warp direction) or perpendicular to it (pick direction). Popular air-jet looms predominantly present defects such as end-outs (missing or broken warp yarns), stubs (excess yarn) and mispicks (missing or broken pick yarns). All these defects have been successfully segmented as illustrated in the accompanying FIGURES. This algorithm has been evaluated with some of the less commonly occurring defects, which are caused by machine malfunction, such as holes in FIG. 13 and oil spots in FIG. 14.

Moreover, the method and system disclosed herein are also useful in detecting defects in opaque textured materials like timber, metal, plastic, etc. illuminated with front lightning.

The filtering and feature extraction operations account for most of the computational requirements. These operations, suitable for parallel computing, require a high performance digital signal processor. An example processor is TMS320C80. Notably, real Gabor functions have also been implemented using cellular neural networks (CNN's). The advantage of CNNs is that they can be implemented using analog VLSI alongside photosensors (CMOS or CCD array) integrated with camera hardware. Thus the real Gabor function filtered outputs can be read off the chip directly. This approach drastically relieves the computational bottleneck and makes the use of DSP processor redundant in alternative embodiments of the invention.

A technique for the automated visual inspection using multi-channel filtering approach is disclosed. This technique utilizes image fusion for combining features from different channels. Moreover, the technique is susceptible to performance enhancement by varying sensitivity, in presence of yarn impurities and low spatial sampling rate. Furthermore, considerable computational saving are enabled by the disclosed technique. These computational savings are attributed to the use of real Gabor function, smaller filter masks, and better local energy functions.

This technique is susceptible to various applications including quality assurance methods for inspecting a surface of an object for defects against a texture background in uniform and textured web products using automated visual inspection. Possible steps include imaging a web material to obtain an image; detecting, automatically, at least one frequency component associated with the background texture of a reference image; applying a pre-designed set of real Gabor function based filters associated with the at least one frequency component and a mask parameter to evaluate features of the image under inspection and generate a plurality of derived images corresponding to the pre-designed set of real Gabor function based filters; estimating energy in a local region by computing a local energy function from at least one of the plurality of derived images to generate a blob-detecting image; combining at least two blob-detecting images with the aid of an image fusion rule to obtain a resultant image; and thresholding the resultant image to further segment at least one defect. In addition, the aforementioned steps benefit from employing image fusion using Bernoulli's rule of combination; generating a set of pixels corrected for illumination irregularities; using a rectified sigmoid in the step of estimating energy to enable tuning and in particular adjusting $\beta$ to be 0.3 in the course of tuning the local energy function.

It will be appreciated that the various features described herein may be used singly or in any combination thereof. Thus, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention as defined in the accompanying claims. In particular, it will be clear to those skilled in the art that the present invention may be embodied in other specific forms, structures, and arrangements, and with other elements, and components, without departing from the spirit or essential characteristics thereof. One skilled in the art will appreciate that the invention may be used with many modifications of structure, arrangement, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being indicated by the appended claims, and not limited to the foregoing description.

We claim:

1. A quality assurance method for inspecting a surface of an object for defects against a texture background in uniform and textured web products using automated visual inspection comprising the steps of:

imaging a web material to obtain an image;

detecting, automatically, at least one frequency component associated with the background texture of a reference image;

applying a pre-designed set of real Gabor function based filters associated with the at least one frequency component and a mask parameter to evaluate features of the image under inspection and generate a plurality of derived images corresponding to the pre-designed set of real Gabor function based filters;

estimating energy in a local region by computing a local energy function from at least one of the plurality of derived images to generate a blob-detecting image;

combining at least two blob-detecting images with the aid of an image fusion rule to obtain a resultant image; and thresholding the resultant image to further segment any possible defect(s).

2. The method according to claim 1 wherein the combining step employs image using Bernoulli's rule of combination.

3. The method according to claim 1 wherein the combining step further employs image fusion using vector addition of pixels.

4. The method according to claim 1 wherein the step of imaging includes generating a set of pixels corrected for illumination irregularities.

5. The method of claim 1 wherein the local energy function is a rectified sigmoid in the step of estimating energy.

6. The method of claim 5 wherein the rectified sigmoid is tuned by adjusting $\beta$ in the range 0.2–0.3.

7. The method according to claim 1, wherein image correction compensates for illumination irregularities by comparison with a reference.

8. The method according to claim 1, further including the step of computing the threshold by estimating at least one maximum value for a pixel in an integrated image generated from the reference image.

9. The method according to claim 1 wherein the surface under inspection is that of a textile.

10. The method according to claim 1 wherein the surface under inspection is that of wood.

11. The method according to claim 1 wherein the surface under inspection is that of a metal.

12. The method according to claim 1 wherein the surface under inspection is that of a paper.

13. The method according to claim 1 wherein the mask parameter is 5×5.

14. The method according to claim 1, wherein the mask parameter is 9×9.

15. The method according to claim 1, wherein the mask parameter is 7×7.

16. A method for quality assurance in uniform and textured web products with known yarn density using automated visual inspection comprising the steps of:

imaging a web material to obtain an image of a surface;

applying a pre-designed Gabor filter to the image to generate a filtered image;

applying a nonlinear function to a pixel in the filtered image to generate a resultant image; and thresholding the resultant image to segment at least one defect.

17. The method according to claim 16, wherein the nonlinear function is a median filter.

18. The method according to claim 16, wherein the nonlinear function is a squaring function.

19. The method according to claim 16, wherein computing the threshold includes estimating a maximum value for a pixel in an integrated image generated from a defect-free web material.

20. The method according to claim 16, wherein the surface is a textile surface.

21. The method according to claim 16, wherein the surface is a wood surface.

22. The method according to claim 16, wherein the surface is a metal surface.

23. The method according to claim 16, wherein the surface is a paper surface.

24. A method for quality assurance in uniform and textured web products with known yarn density using automated visual inspection comprising the steps of:

imaging a defect-free web material by generating a set of pixels corrected for illumination irregularities to obtain an image;

selecting at least one frequency component associated with the background texture of the image;

designing at least one real Gabor function based filter using the at least one frequency component associated with the background texture of the image; and computing, automatically, a threshold associated with the at least one real Gabor function based filter using the image.

25. The method according to claim 24 wherein image correction compensates for illumination irregularities by comparison with a reference.

26. The method according to claim 24 wherein the step of selecting includes automatically determining the at least one frequency component associated with the background texture of the image from a set of pixels in the warp direction whereby reducing the need for manual tuning.

27. The method according to claim 24 wherein the mask parameter is 5×5.

28. The method according to claim 24 wherein the mask parameter is 9×9.

29. The method according to claim 24 wherein the mask parameter is 7×7.

30. The method according to claim 24 wherein the surface under inspection is that of a textile.

31. A method for quality assurance in the uniform and textured web products using automated visual inspection comprising the steps of:

imaging a defect-free web material by generating a set of pixels corrected for illumination irregularities to obtain an image;

detecting, automatically, a first frequency component associated with the background texture of the image from a set of pixels in the warp direction and a second frequency component associated with the background texture of the image from a set of pixels in the weft direction;

selecting a highest frequency component following comparison of at least the first and the second frequency components;

designing at least one real Gabor function based filter using the selected frequency component associated with the background texture of the image; and computing, automatically, a threshold associated with the at least one real Gabor function based filter using the image.

32. The method according to claim 31, wherein image correction compensates for illumination irregularities by comparison with a reference.

33. The method according to claim 31, wherein the surface under inspection is that of a textile.

34. The method according to claim 31, wherein the step of computing the threshold includes estimating a maximum value for a pixel in an integrated image generated from the defect-free web material.

35. The method of claim 34 wherein the integrated image is generated from a plurality of real Gabor functions that include the at least one real Gabor function.

36. A system for automatically detecting defects against a textured background in a surface of a material, the system comprising:

image acquisition means;

at least one processor configured to execute the steps for detecting, automatically, at least one frequency component associated with the background texture of a reference image, applying a pre-designed set of real Gabor function based filters associated with the at least one frequency component and a mask parameter to evaluate features of the image under inspection and generate a plurality of derived images corresponding to the pre-designed set of real Gabor function based filters, estimating energy in a local region by computing a local energy function from at least one of the plurality of derived images to generate a blob-detecting image, combining at least two blob-detecting images with the aid of an image fusion rule to obtain a resultant image, and thresholding the resultant image to further segment any possible defect(s); and a memory for storing at least one mean and standard deviation value for a blob detecting image, and at least one threshold based on a defect-free image.

* * * * *